(12) United States Patent
Miura et al.

(10) Patent No.: US 7,937,227 B2
(45) Date of Patent: May 3, 2011

(54) METHOD, APPARATUS, PROGRAM, AND RECORDING MEDIUM FOR EVALUATING ULTRAVIOLET RADIATION PROTECTION EFFECT

(75) Inventors: Yoshimasa Miura, Yokohama (JP); Masato Hatao, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 12/682,286

(22) PCT Filed: Oct. 17, 2008

(86) PCT No.: PCT/JP2008/068851
§ 371 (c)(1),
(2), (4) Date: Apr. 9, 2010

(87) PCT Pub. No.: WO2009/051222
PCT Pub. Date: Apr. 23, 2009

(65) Prior Publication Data
US 2010/0256924 A1 Oct. 7, 2010

(30) Foreign Application Priority Data
Oct. 18, 2007 (JP) .................................. 2007-271743

(51) Int. Cl.
G06F 17/40 (2006.01)
G06F 17/00 (2006.01)
(52) U.S. Cl. .............. 702/30; 702/32; 702/19; 250/372; 356/51
(58) Field of Classification Search .............. 702/30, 702/32, 19, 76
See application file for complete search history.

(56) References Cited

U.S. PATENT DOCUMENTS

| | | | |
|---|---|---|---|
| 5,365,068 A * | 11/1994 | Dickerson | 250/372 |
| 5,500,533 A | 3/1996 | Ogawa et al. | |
| 5,640,957 A * | 6/1997 | Kaminski et al. | 600/407 |
| 5,824,320 A | 10/1998 | Rouillard et al. | |
| 6,862,542 B2 * | 3/2005 | Lockhart et al. | 702/76 |
| 2004/0195519 A1 | 10/2004 | Refregier et al. | |
| 2005/0036961 A1 | 2/2005 | Hansenne et al. | |

FOREIGN PATENT DOCUMENTS

JP 07-167781 7/1995
(Continued)

OTHER PUBLICATIONS

Iveson R D, et al., A study of the effect of anatomical site on sun protection factor efficiency using a novel UV delivery device, Journal of Cosmetic Science, 1995. 10, vol. 46, No. 5, p. 271-280.
(Continued)

Primary Examiner — Hal D Wachsman
(74) Attorney, Agent, or Firm — IPUSA, PLLC

(57) ABSTRACT

A method and apparatus for evaluating an ultraviolet radiation protection effect in a measurement sample is used for evaluating SPF (Sun Protection Factor). First, a temporal change of the spectral transmission spectrum in the measurement sample within a predetermined light wavelength range at predetermined wavelength intervals is measured. Second, a correlation between a light irradiating time and minimal erythema doses by predetermined lime intervals based on the temporal change of the spectral transmission spectrum is set. Third a predicted in vitro SPF in the measurement sample using a time until an accumulated minimal erythema dose that is obtained as a time integration of the minimal erythema doses based on the correlation obtained in the second step reaches 1 MED (Minimum Erythema Dose) is calculated.

15 Claims, 17 Drawing Sheets

FOREIGN PATENT DOCUMENTS

| | | |
|---|---|---|
| JP | 09-506906 | 7/1997 |
| JP | 2003-073250 | 3/2003 |
| JP | 2005-060395 | 3/2005 |

OTHER PUBLICATIONS

Reece B T, et al., An in vitro method for screening sunscreen formulations for sun protection factor using a full-thickness skin model, Journal of Cosmetic Science, 1992. 12, vol. 43, No. 6, p. 307-312.
Journal of the Society of Cosmetic Chemists (1989) 40:33, 127-133.
CIE Journal (1987) 6:1, 17-22.
Method for the In Vitro Determination of UVA Protection Provided by Sunscreen Products, 2007, pp. 1-21.
Skin Pharmacology and Physiology 2007; 20: 57-64.
Extended European search report mailed Dec. 22, 2010, 11 pages.
J.W.Stanfield:"Optimizing in vitro Measurement of Sunscreen Protection", SÖFW-Journal, vol. 132, No. 7, 2006, pp. 19-23, XP008129662.
Couteau et al: "Study of the photostability of 18 sunscreens in creams by measuring the SPF in vitro", Journal of Pharmaceutical and Biomedical Analysis, New York, NY, US, vol. 44, No. 1, Apr. 13, 2007, pp. 270-273, XP022026240.
Miura Yoshimasa et al: "Algorithm for in vitro Sun Protection Factor Based on Transmission Spectrum Measurement with Concomitant Evaluation of Photostability", Photochemistry and Photobiology, vol. 84, No. 6, Jul. 4, 2008, pp. 1569-1575, XP002611522.
Sayre R M et al: "Photostability Testing of Avobenzone", Cosmetics & Toiletries, Wheaton, IL, US, vol. 114, No. 5, May 1, 1999, XP009014805, 5 pages.
Sayre Robert M et al: "In Vitro Sunscreen Transmittance Measurement with Concomitant Evaluation of Photostability: Evolution of a Method", Photochemistry and Photobiology, vol. 85, No. 4, Jul. 2009, pp. 1038-1040, XP002611523.
Miura Yoshimasa et al; "Response to Comments by Sayra, Dowdy and Stanfield on our Article Entitled "Algorithm for in vitro Sun Protection Factor Based on Transmission Spectrum Measurement with Concomitant Evaluation of Photostabllity. "Photochem. Photobiol. (2008)", Photochemistry and Photobiology, vol. 85, No. 4, Jul. 2009, pp. 1041-1042, XP002611524.

* cited by examiner

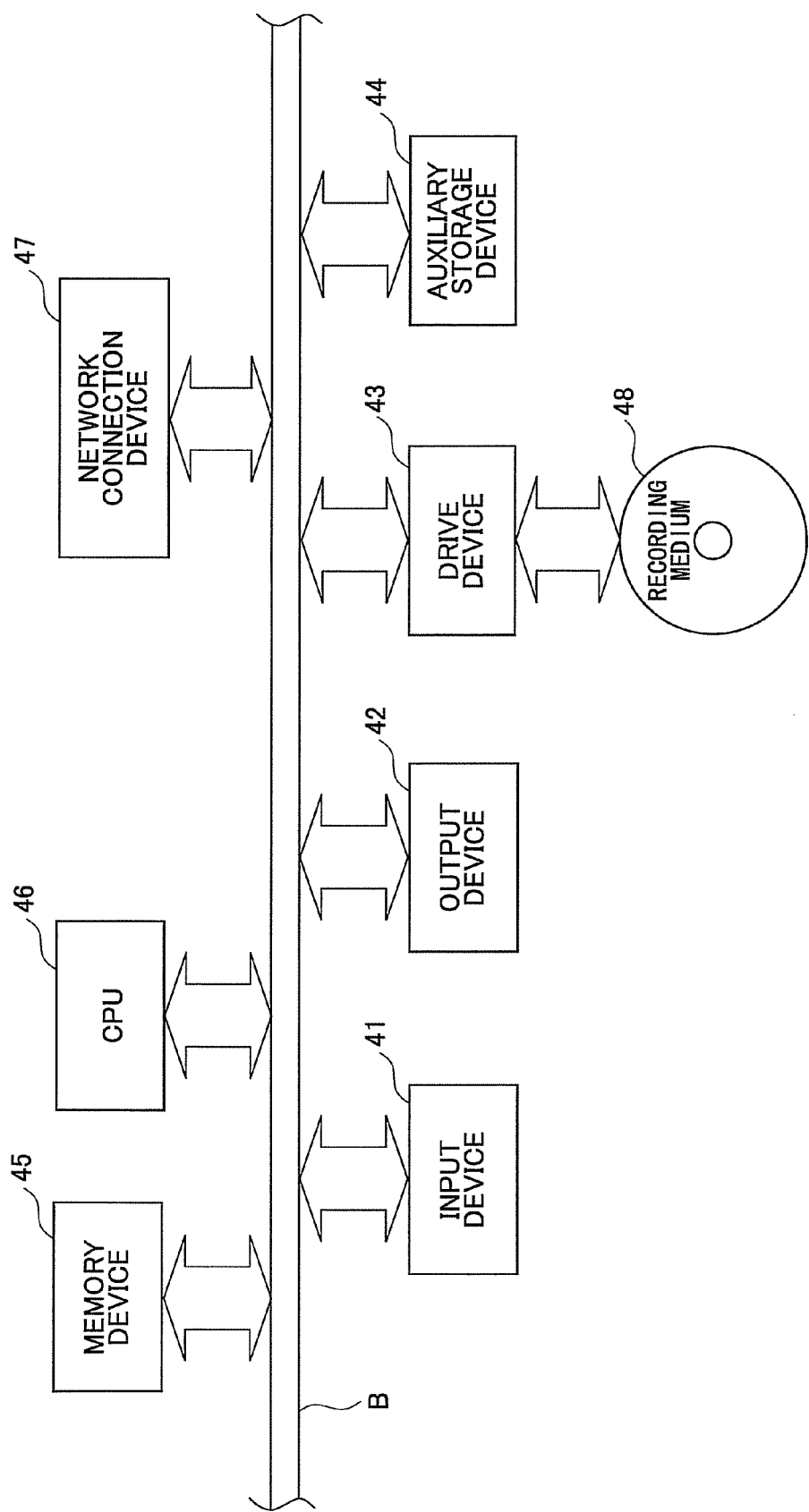

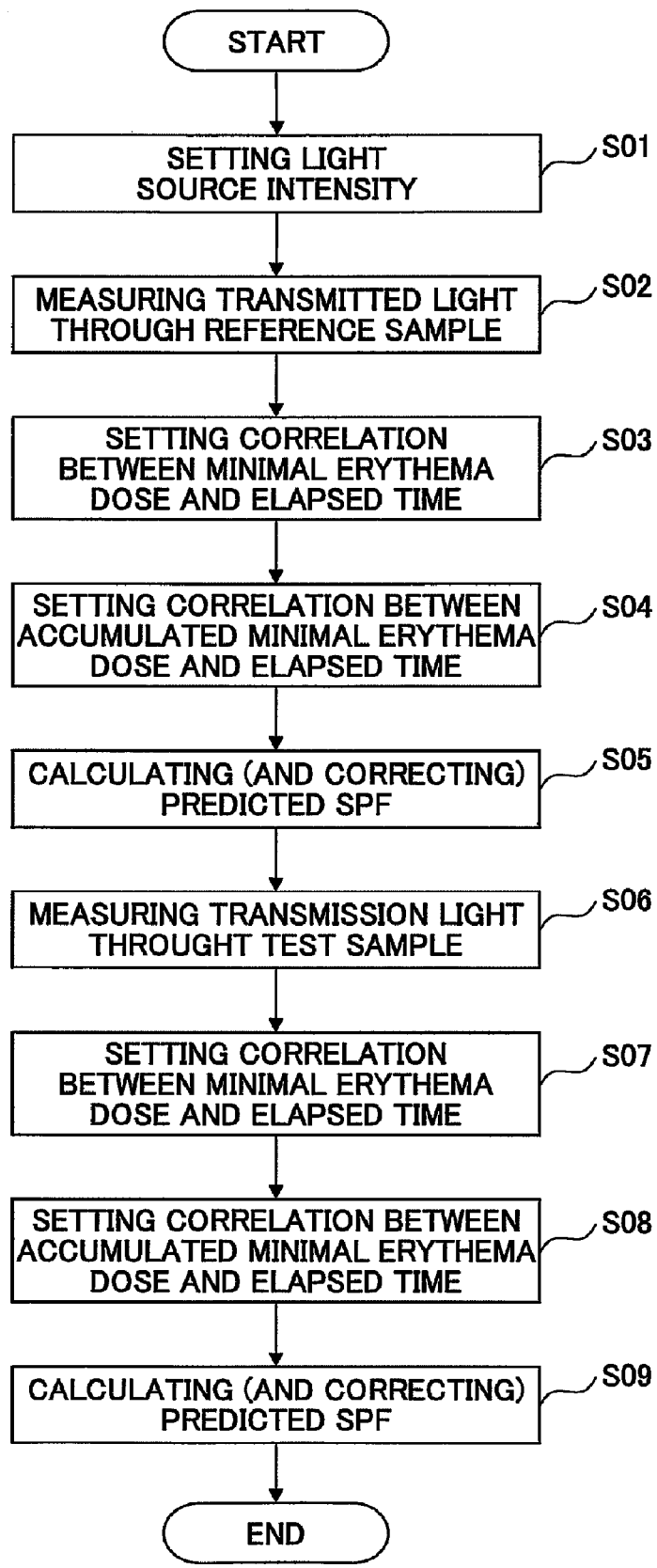

FIG.5C

| TIME (MIN) | MINIMAL ERYTHEMA DOSE | ACCUMULATED MINIMAL ERYTHEMA DOSE |
|---|---|---|
| 1 | 0.7436 | 0.7436 |
| 2 | 0.7391 | 1.4827 |
| 3 | 0.7346 | 2.2173 |
| 4 | 0.7301 | 2.9474 |
| 5 | 0.7256 | 3.673 |
| 6 | 0.7211 | 4.3941 |
| 7 | 0.7166 | 5.1107 |
| 8 | 0.7121 | 5.8228 |
| 9 | 0.7076 | 6.5304 |
| 10 | 0.7031 | 7.2335 |
| 11 | 0.6986 | 7.9321 |
| 12 | 0.6941 | 8.6262 |
| 13 | 0.6896 | 9.3158 |
| 14 | 0.6851 | 10.0009 |
| 15 | 0.6806 | 10.6815 |

FIG.6C

| TIME (MIN) | MINIMAL ERYTHEMA DOSE | ACCUMULATED MINIMAL ERYTHEMA DOSE |
|---|---|---|
| 1 | 0.084 | 0.084 |
| 2 | 0.0879 | 0.1719 |
| 3 | 0.0918 | 0.2637 |
| 4 | 0.0957 | 0.3594 |
| 5 | 0.0996 | 0.459 |
| 6 | 0.1035 | 0.5625 |
| 7 | 0.1074 | 0.6699 |
| 8 | 0.1113 | 0.7812 |
| 9 | 0.1152 | 0.8964 |
| 10 | 0.1191 | 1.0155 |
| 11 | 0.123 | 1.1385 |
| 12 | 0.1269 | 1.2654 |
| 13 | 0.1308 | 1.3962 |
| 14 | 0.1347 | 1.5309 |
| 15 | 0.1386 | 1.6695 |

FIG.7C

| TIME (MIN) | MINIMAL ERYTHEMA DOSE | ACCUMULATED MINIMAL ERYTHEMA DOSE |
|---|---|---|
| 1 | 0.0243903 | 0.0243903 |
| 2 | 0.0243806 | 0.0487709 |
| 3 | 0.0243709 | 0.0731418 |
| 4 | 0.0243612 | 0.097503 |
| 5 | 0.0243515 | 0.1218545 |
| 6 | 0.0243418 | 0.1461963 |
| 7 | 0.0243321 | 0.1705284 |
| 8 | 0.0243224 | 0.1948508 |
| 9 | 0.0243127 | 0.2191635 |
| 10 | 0.024303 | 0.2434665 |
| 11 | 0.0242933 | 0.2677598 |
| 12 | 0.0242836 | 0.2920434 |
| 13 | 0.0242739 | 0.3163173 |
| 14 | 0.0242642 | 0.3405815 |
| 15 | 0.0242545 | 0.364836 |

METHOD, APPARATUS, PROGRAM, AND RECORDING MEDIUM FOR EVALUATING ULTRAVIOLET RADIATION PROTECTION EFFECT

STATEMENT OF CONTINUING DATA

The instant application is a National Phase application under 35 USC 371 of the international application PCT/JP2008/068851 filed on Oct. 17, 2008, which is based on Japanese Priority Application No. 2007-271743 filed on Oct. 18, 2007.

TECHNICAL FIELD

The present invention relates to an ultraviolet radiation protection effect evaluation method, an ultraviolet radiation protection effect evaluation apparatus, an ultraviolet radiation protection effect evaluation program and a recording medium having ultraviolet radiation protection effect evaluation program recorded on it. More specifically, it relates to an ultraviolet radiation protection effect evaluation method, an ultraviolet radiation protection effect evaluation apparatus, an ultraviolet radiation protection effect evaluation program and a recording medium having ultraviolet radiation protection effect evaluation program recorded on it, which enable accurate evaluation of the ultraviolet radiation protection effect even for samples having high SPF.

BACKGROUND ART

Conventionally, the SPF (Sun Protection Factor) is used as a scale representing the ultraviolet radiation protection effect of cosmetic products for preventing sunburn due to ultraviolet radiation (so-called sun protection products). This SPF, which is an index indicating the effect of skin protection from sunburn due to ultraviolet radiation and sunburn prevention, is defined by a value obtained by dividing the amount of ultraviolet radiation necessary for causing slight redness in the case of using a sun protection product by the amount of ultraviolet radiation necessary for causing slight redness in the case of not using a sun protection product. This means that with, for example, a sun protection product of SPF 10, the same sunburn (erythema) as that on bare skin is caused by exposure to ten times as much ultraviolet radiation as in the case of causing sunburn on bare skin.

In measuring the SPF, artificial light (a solar simulator) very much like sunlight is adopted in place of sunlight that may vary in value depending on the season or location. The measurement is performed by exposing each of unprotected skin and protected skin to a certain amount of ultraviolet radiation and determining the next day whether erythema has been caused.

Using the SPF measured based on the above-described method makes it possible to objectively evaluate the ultraviolet radiation protection effect of sun protection products. However, the above-described method necessitates cooperation of a large number of volunteers of specific skin types. Therefore, tremendous amounts of money and time are required. Accordingly, it has been desired to develop an in vitro and simple method of calculating in vitro predicted SPF having high correlation with the in vivo SPF obtained by the above-described method for, for example, evaluation of the ultraviolet radiation protection effect of a product under development.

Conventionally, known methods of evaluating an ultraviolet radiation protection effect by in vitro measurement includes a dilution method that measures the ultraviolet radiation absorbance or transmittance of a sample diluted with an organic solvent in a quartz cell and a thin film method that measures the ultraviolet radiation absorbance or transmittance of a sample formed into a film having even thickness on a quartz plate. These conventional methods are significant in understanding characteristics such as the absorption maximum wavelength and a protection wavelength range of an ultraviolet absorber, but may not predict the SPF. This is because these methods for evaluating an ultraviolet radiation protection effect greatly differ from methods for measuring in vivo SPF. Further, the biological reaction represented by the SPF depends on the ultraviolet wavelength, and the erythema reaction is likely to occur at some ultraviolet wavelengths and is less likely to occur at other ultraviolet wavelengths. Therefore, it has been considered necessary to take the effect on a living body into consideration on a wavelength basis.

With respect to the above-described two problems, Non-Patent Document 1, Journal of the Society of Cosmetic Chemists (1989) 40:33, 127-133 applies a sample on a medical tape serving as a skin substitute film and measures the spectral transmission spectrum of the sample. This measurement result is calculated using the Diffey & Robson formula to obtain the SPF. This Diffey & Robson formula has successfully solved the above-described problems by dealing with the wavelength dependence of the erythema reaction as a human biological reaction by using an erythema factor (tendency to redness) disclosed in Non-Patent Document 2, CIE Journal (1987) 6:1, 17-22.

However, in vivo SPF includes various factors such as an individual difference, a regional difference, an age difference, a gender difference and a skin type difference. Therefore, there still exists a problem that it is actually very difficult to predict the SPF with accuracy based only on the single example of the erythema factor.

Therefore, an evaluation method has been proposed that may predict in vitro SPF of even unknown samples not by adopting only the erythema factor but by deriving an arithmetic expression enabling to obtain statistically high correlation from the relationship between a large number of samples with known in vivo SPF and their spectral transmission spectra (See, for example, Patent Document 1, Journal of the Society of Cosmetic Chemists (1989) 40:33, 127-133). This evaluation method makes it possible to obtain in vitro predicted SPF with accuracy and has eliminated variation factors arising from an individual difference, a regional difference, an age difference, a gender difference, a skin type difference, etc. The Non-Patent Document 1 referred to is B. L. Diffey and J. Robson, "A new substrate to measure sunscreen protection factors throughout the ultraviolet spectrum", *Journal of the Society of Cosmetic Chemists*, Vol 40, pages 127-133 (May/June 1989). The Non-Patent Document 2 referred to is A. F. McKinlay and B. L. Diffey, "A REFERENCE ACTION SPECTRUM FOR ULTRAVIOLET INDUCED ERYTHEMA IN HUMAN SKIN", CIE RESEARCH NOTE, *CIE Journal*, Vol. 6, No. 1, 1987, pages 17-22. The patent document referred to is Japanese Patent No. 3337832.

DISCLOSURE OF THE INVENTION

Problems to be Solved by the Invention

However, the method of evaluating an ultraviolet radiation protection effect disclosed in Patent Document 1, Journal of the Society of Cosmetic Chemists (1989) 40:33, 127-133 described above has a problem in that it is possible to make accurate predictions up to approximately SPF 30 but not possible to make accurate predictions with respect to samples of SPF 30 or higher SPF. In recent years, mainstream products have SPF 50 or higher SPF, and products having yet higher SPF are expected to be launched in the future.

In recent years, there have been many findings on a photodegradation phenomenon of an ultraviolet absorber due to ultraviolet light. Therefore, reproducing light irradiating conditions same as conditions for measuring in vivo SPF and thereby correctly estimating a corresponding decrease in the SPF are considered necessary for accurate prediction of the SPF in the method of calculating in vitro SPF predicted values as well.

The present invention is provided in view of the above-described points, and has an object of providing a method of evaluating an ultraviolet radiation protection effect based on in vitro measurement, which method reflects the photodegradation phenomenon of a sample due to irradiated light and demonstrates a high correlation with the in vivo SPF even in samples with high SPF, and an apparatus for evaluating an ultraviolet radiation protection effect using this method.

Means for Solving Problems

Embodiments of the present invention may provide various steps and units described below.

According to an aspect of the present invention, there is provided an evaluating method for evaluating an ultraviolet radiation protection effect in a measurement sample including a first step of measuring a temporal change of the spectral transmission spectrum in the measurement sample within a predetermined wavelength range at predetermined wavelength intervals by irradiating with light including ultraviolet radiation from a light source under a predetermined light irradiating condition, a second step of setting a correlation between a light irradiating time and minimal erythema doses by predetermined time intervals based on the temporal change of the spectral transmission spectrum obtained in the first step, a third step of calculating a predicted in vitro SPF in the measurement sample using a time until an accumulated minimal erythema dose that is obtained as a time integration of the minimal erythema doses based on the correlation obtained in the second step reaches 1 MED. With this, it is possible to reflect a photodegradation phenomenon caused by irradiated light on the evaluation, and realize evaluation of an ultraviolet radiation protection effect in the measurement sample having a large SPF with high accuracy.

Further, in the first step, it is preferable to measure the temporal change of the spectral transmission spectrum at predetermined time intervals. With this, by arbitrarily setting the predetermined time intervals, it is possible to easily adjust a processing time or the like. Therefore, the processing time necessary for the evaluation may be shortened when necessary.

Further, in the first step, it is preferable to measure the temporal change of the spectral transmission spectrum caused by photodegradation of the spectral transmission spectrum. With this, it is possible to reflect the photodegradation of the sample caused by irradiated light on the evaluation, and calculate a predicted in vitro SPF with high accuracy.

Further, in the third step, it is preferable that the predicted in vitro SPF in the measurement sample is calculated using a time until an accumulated minimal erythema dose that is obtained as a time integration of the minimal erythema doses based on the correlation obtained in the second step reaches 1 MED, and the predicted SPF in the measurement sample is corrected using at least one of data of the predicted SPF, light source intensity of the light source, and an application quantity of the measurement sample applied on a skin substitute film. With this, it is possible to calculate a predicted in vitro SPF which matches well an in vivo SPF with high accuracy by correcting the predicted SPF calculated above using at least one of a predicted in vitro SPF obtained using a reference sample, light source intensity, and a sample application quantity.

Further, in the third step, it is preferable to apply a liquid material having a transmittance of 50% or more on the skin substitute film at least in the predetermined wavelength range in the first step to be used as the reference sample. With this, it is possible to improve accuracy of the evaluation by using the reference sample not only as the skin substitute film but also as a blank of the measurement sample.

Further, in the third step, it is preferable to use a sample of which in vivo SPF is known is used as the reference sample at least in the predetermined wavelength range in the first step. With this, it is possible to improve accuracy of the evaluation by using the sample of which in vivo SPF is known as the reference sample.

Further, in the third step, it is preferable to calculate 1 MED based on light source intensity when the predetermined light irradiating condition is that the light irradiates only from the light source. With this, it is possible to reflect photodegradation of the sample caused by the ultraviolet radiation on the evaluation, and evaluate a predicted in vitro SPF with high accuracy.

According to another aspect of the invention, there is provided an evaluating apparatus that evaluates an ultraviolet radiation protection effect in a measurement sample, the evaluating apparatus including a temporal change measurement unit configured to measure a temporal change of a spectral transmission spectrum in the measurement sample within a predetermined wavelength range at predetermined wavelength intervals by irradiating with light including ultraviolet radiation from a light source under a predetermined light emission condition, a correlation setting unit configured to set a correlation between a light irradiating time and minimal erythema doses by predetermined time intervals based on the temporal change of the spectral transmission spectrum obtained by the temporal change measurement unit, and a predicted SPF calculation unit configured to calculate a predicted in vitro SPF in the measurement sample using a time until an accumulated minimal erythema dose that is obtained as a time integration of the minimal erythema doses based on the correlation obtained by the correlation setting unit reaches 1 MED. With this, it is possible to reflect a photodegradation phenomenon caused by irradiated light on the evaluation, and realize evaluation of an ultraviolet radiation protection effect in the measurement sample having a large SPF with high accuracy.

Further, in the temporal change measurement unit, it is preferable to measure the temporal change of the spectral transmission spectrum at predetermined time intervals. With this, by arbitrarily setting the predetermined time intervals, it is possible to easily adjust a processing time or the like. Therefore, the processing time necessary for the evaluation may be shortened when necessary.

Further, in the temporal change measurement unit, it is preferable to measure the temporal change of the spectral transmission spectrum caused by photodegradation of the spectral transmission spectrum. With this, it is possible to reflect the photodegradation of the sample caused by irradiated light on the evaluation, and calculate a predicted in vitro SPF with high accuracy.

Further, in the predicted SPF calculation unit, it is preferable that the predicted in vitro SPF in the measurement sample is calculated using a time until an accumulated minimal erythema dose that is obtained as a time integration of the minimal erythema doses based on the correlation obtained by the correlation setting unit reaches 1 MED, and the predicted SPF in the measurement sample is corrected using at least one of data of the predicted SPF, light source intensity of the light source, and an application quantity of the measurement sample applied on a skin substitute film. With this, it is possible to calculate a predicted in vitro SPF which matches well an in vivo SPF with high accuracy by correcting the predicted SPF calculated above using at least one of a predicted in vitro SPF obtained using a reference sample, light source intensity, and a sample application quantity.

Further, in the predicted SPF calculation unit, it is preferable to apply a liquid material having a transmittance of 50% or more on the skin substitute film at least in the predetermined wavelength range used in the temporal change measurement unit in order to be used as the reference sample. With this, it is possible to improve accuracy of the evaluation by using the reference sample not only as the skin substitute film but also as a blank of the measurement sample.

Further, in the predicted SPF calculation unit, it is preferable to use a sample, for which in vivo SPF is known, and this sample is used as the reference sample at least in the predetermined wavelength range used in the temporal change measurement unit. With this, it is possible to improve accuracy of the evaluation by using the sample, for which in vivo SPF is known, as the reference sample.

Further, in the predicted SPF calculation unit, it is preferable to calculate 1 MED based on light source intensity when the predetermined light irradiating condition is that the light irradiates only from the light source. With this, it is possible to reflect photodegradation of the sample caused by the ultraviolet radiation on the evaluation, and evaluate a predicted in vitro SPF with high accuracy.

According to another aspect of the invention, there is provided an evaluating computer program that evaluates an ultraviolet radiation protection effect in a measurement sample, the evaluating computer program representing a sequence of instructions, which when executed by a computer, the instructions cause the computer to perform a first step of measuring a temporal change of the spectral transmission spectrum in the measurement sample within a predetermined wavelength range at predetermined wavelength intervals by irradiating with light including ultraviolet radiation from a light source under a predetermined light irradiating condition, a second step of setting a correlation between a light irradiating time and minimal erythema doses by predetermined time intervals based on the temporal change of the spectral transmission spectrum obtained in the first step, a third step of calculating a predicted in vitro SPF in the measurement sample using a time until an accumulated minimal erythema dose that is obtained as a time integration of the minimal erythema doses based on the correlation obtained in the second step reaches 1 MED. With this, it is possible to reflect a photodegradation phenomenon caused by irradiated light on the evaluation, and realize evaluation of an ultraviolet radiation protection effect in the measurement sample having a large SPF with high accuracy. Further, it is possible to easily realize the evaluation of the ultraviolet radiation protection effect in the present invention using a general-purpose personal computer with the evaluating computer program or the like installed on it.

According to another aspect of the invention, there is provided a computer-readable medium storing an evaluating computer program that evaluates an ultraviolet radiation protection effect in a measurement sample, the evaluating computer program representing a sequence of instructions, which when executed by a computer, the instructions cause the computer to perform a first step of measuring a temporal change of the spectral transmission spectrum in the measurement sample within a predetermined wavelength range at predetermined wavelength intervals by irradiating with light including ultraviolet radiation from a light source under a predetermined light irradiating condition, a second step of setting a correlation between a light irradiating time and minimal erythema doses by predetermined time intervals based on the temporal change of the spectral transmission spectrum obtained in the first step, a third step of calculating a predicted in vitro SPF in the measurement sample using a time until an accumulated minimal erythema dose that is obtained as a time integration of the minimal erythema doses based on the correlation obtained in the second step reaches 1 MED. With this, it is possible to reflect a photodegradation phenomenon caused by irradiated light on the evaluation, and realize evaluation of an ultraviolet radiation protection effect in the measurement sample having a large SPF with high accuracy. Further, it is possible to easily realize the evaluation of the ultraviolet radiation protection effect in the present invention using a general-purpose personal computer with the evaluating computer program or the like installed on it.

Effect of the Invention

According to the embodiment of the present invention, it is possible to accurately evaluate an ultraviolet radiation protection effect using in vitro measurement, which has a high correlation with in vivo SPF even for samples having high SPF, by reflecting the photodegradation phenomenon of the samples caused due to irradiated light.

BRIEF DESCRIPTION OF DRAWINGS

FIG. 3 illustrates a hardware structure enabling an evaluation process of the embodiment of the present invention, as an example.

FIG. 4 illustrates an evaluation procedure of an ultraviolet radiation protection effect of the embodiment of the present invention, as an example.

FIG. 5C illustrates a minimal erythema dose and an accumulated minimal erythema dose of the reference sample converted into data of every one minute.

FIG. 6C illustrates a minimal erythema dose and an accumulated minimal erythema dose of the test sample A converted into data of every one minute.

FIG. 7C illustrates a minimal erythema dose and an accumulated minimal erythema dose of test sample B converted into data of every one minute.

EXPLANATION OF REFERENCE SYMBOLS

Figure 1:
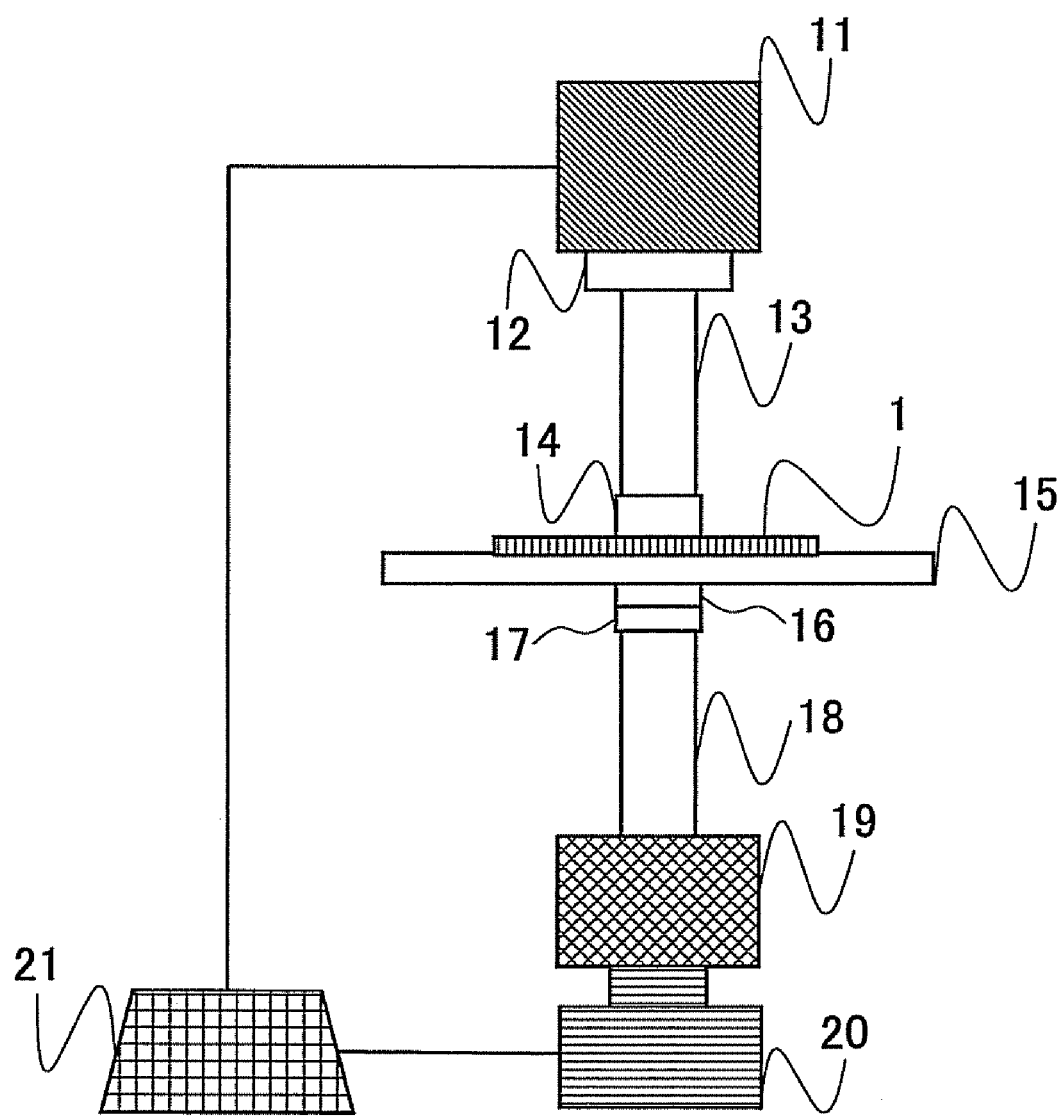
FIG. 1 is a diagram illustrating a schematic configuration of an ultraviolet radiation protection effect evaluation apparatus of an embodiment, as an example.

1: Sample
10: Evaluating apparatus
11: Light source
12: Filter
13: First optical fiber
14: Irradiation port
15: Measurement sample substrate
16: Integrating sphere
17: Detection port
18: Second optical fiber
19: Spectrometer
20: Photodetector
21: Computer
31: Input unit
32: Output unit
33: Storage unit
34: Temporal change measuring unit
35: Correlation setting unit
36: Predicted SPF calculation unit
37: Control unit
41: Input device
42: Output device
43: Drive device
44: Auxiliary storage device
45: Memory device
46: CPU
47: Network connection device
48: Recording medium

BEST MODE FOR CARRYING OUT THE INVENTION

A preferred embodiment of an ultraviolet radiation protection effect evaluation method, an ultraviolet radiation protection effect evaluation apparatus, an ultraviolet radiation protection effect evaluation program and a recording medium having the ultraviolet radiation protection effect evaluation program recorded on it is described in reference to figures.
<Structural Example of the Ultraviolet Radiation Protection Effect Evaluation Apparatus>

FIG. 1 is a diagram illustrating a schematic configuration of an ultraviolet radiation protection effect evaluation apparatus of this embodiment, as an example.

The ultraviolet radiation protection effect evaluation apparatus 10 illustrated in FIG. 1 is an apparatus for measuring a sample 1 (a reference sample or a measurement sample to be tested). The ultraviolet radiation protection effect evaluation apparatus 10 includes a light source 11, a filter 12, a first optical fiber 13, an irradiation port 14, a measurement sample substrate 15, an integrating sphere 16, a detection port 17, a second optical fiber 18, a spectrometer 1, a photodetector 20 and a computer 21.

The light source 11 is preferably a xenon lamp, which irradiates a white light including ultraviolet radiation, visible radiation, and infrared radiation. However, the light source 11 is not limited to this. Further, the xenon lamp, which is a white light source, can be used as simulated sunlight.

The filter 12 is positioned in the vicinity of the light source 11 in a light travelling direction from the light source 11, and corrects the ultraviolet radiation spectrum of a light beam irradiating from the light source 11.

A first optical fiber 13 is positioned in the vicinity of the filter 12 in the light travelling direction from the filter 12. The light transmitted through the filter 12 is led to an irradiation port 14.

The above-mentioned light irradiates from the irradiation port 14. The irradiation port 14 and the detection port 17 are fixed while interposing a predetermined interval between these. A sample mounting substrate 15 is fixed to a position apart by a predetermined distance from the irradiation port 14. Said differently, the irradiation port 14, the measurement sample 1, the sample mounting substrate 15 and the integrating sphere 16 are arranged in this order along the light travelling direction.

The sample mounting substrate 15 is a sample support having a structure on which the measurement sample is mounted. The sample mounting substrate 15 preferably has a structure that an outer periphery or a part of the sample 1 is securely held, for example.

The integrating sphere 16 receives and condenses light beams transmitted through the sample 1, and makes the light beams uniform by spatially integrating the light beams. Meanwhile, the integrating sphere 29 may be omitted.

The detection port 17 receives the light beams made uniform by the integrating sphere 29, and guides the light beam to the second optical fiber 18.

The second optical fiber 18 is positioned in the vicinity of the detection port 17 in the light travelling direction from the detection port 17. The second optical fiber 18 guides the light beams received by the detection port 17 into the spectrometer 19.

The spectrometer 19 enables the separation of the light beams from the second optical fiber 18 at predetermined wavelength intervals in a range of 200 nm to 400 nm, which is within the ultraviolet radiation range. The predetermined wavelength intervals are, for example, every 0.5 nm, 1 nm, 5 nm or the like. However, the predetermined wavelength intervals are not limited in the present invention. The following explanation is given on a premise that the predetermined wavelength intervals are measured every 1 nm, as an example. The ultraviolet radiation separated by the spectrometer 19 impinges on the photodetector 20.

The spectrometer 19 is adjusted to have a sensitivity characteristic for ultraviolet radiation. For example, a highly sensitive spectral performance may be demonstrated by using a diffraction grating having an excellent sensitivity characteristic in an ultraviolet radiation range of 200 nm thru 400 nm. Specifically, a concave diffraction grating (model number 10-015) manufactured by Shimadzu Corporation or the like may be used. However, the spectrometer 19 is not limited to this. The number of the spectrometers 19 is one or two, and preferably two.

The photodetector 20 detects the ultraviolet radiation separated by the spectrometer 19 with an optical sensor. The photodetector 20 converts the intensity of the light beams having various wavelengths into signals of electric current or voltage. The current or voltage signals are sent to the computer 21 connected by electrical wiring.

With recent progress in faint light detection techniques, photomultipliers with enhanced detection sensitivity are increasingly used. It is theoretically apparent that photomultipliers have higher detection sensitivity than conventional photodiode arrays and CCDs. However, it is necessary to select a material of the photoelectric surface of the photomultiplier depending on a wavelength range of light to be detected.

As the photodetector 20 serving as the photodetection means, a photomultiplier having a good sensitivity characteristic in, for example, an ultraviolet radiation range of 200 nm to 400 nm realizes a highly sensitive ultraviolet radiation detector. Specifically, a photomultiplier having the photoelectric surface formed of materials selected from elements such as In, Ga, N, Al, O, and Cs may be used.

Not only the photomultiplier but also a semiconductor photodetector made of In, Ga, N, Al, and O may be used as the photodetector 20.

The computer 21 determines spectral intensities at intervals of, for example, 1 nm or the like. The computer 21 calculates a final in vitro predicted SPF for the measurement sample. Further, the computer controls the light source 11 to be turned on or off. Further, the computer 21 is capable of receiving data from the photodetector 20, and processing the data to be changed into a format easily understandable by a user. Then, the result of the changed data can be displayed on a screen, printed out on recording papers, or stored in a storage medium. Further, the computer 21 may be, for example, a general-purpose personal computer. Various functions of the ultraviolet radiation protection effect evaluation apparatus 10 can be carried out by the computer 21 based on instructions from a user through an input unit or the like.

<Functional Configuration of the Ultraviolet Radiation Protection Effect Evaluation Apparatus>

Figure 2:
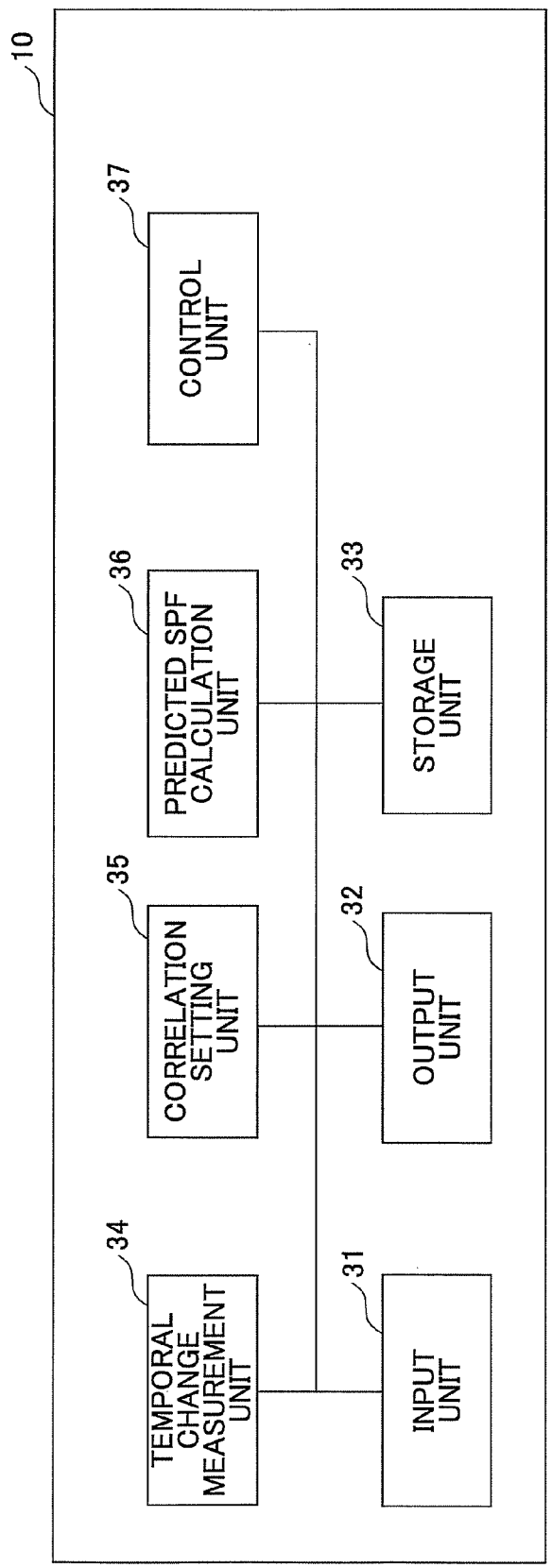
FIG. 2 is a diagram illustrating a functional configuration of the ultraviolet radiation protection effect evaluation apparatus of the embodiment, as an example.

Next, the functional configuration of the ultraviolet radiation protection effect evaluation apparatus 10 is described in reference to the figures. FIG. 2 is a diagram illustrating the functional configuration of the ultraviolet radiation protection effect evaluation apparatus of this embodiment, as an example.

Referring to FIG. 2, the ultraviolet radiation protection effect evaluation apparatus 10 is configured to include an input unit 31, an output unit 32, a storage unit 33, a temporal change measurement unit 34, a correlation setting unit 35, a predicted SPF calculation unit 36 and a control unit 37.

The input unit 31 is provided in, for example, the computer 21, and receives various data such as a user's instruction, which are input in order to start evaluation or cause measurement results to be output by the output unit 32. The input unit 31 is made up of, for example, a keyboard and a pointing device such as a mouse.

The output unit 32 is provided in, for example, the computer 21, and displays or outputs a content input through the input unit 31 or a content of what is executed based on the content of the input. The output unit 32 includes a display, a speaker or the like. Further, the output unit 32 may have functions as a printer. In this case, simple measurement results or calculation results can be printed on printing media such as paper and provided to a user.

The storage unit 33 may be provided in, for example, the computer 21, and stores various data such as results of measurements by the temporal change measurement unit 35, a content set by the correlation setting unit 35, results of calculations obtained by the predicted SPF calculation unit 36 or the like. The storage unit 33 can read out the stored various data when necessary.

The temporal change measurement unit 34 measures the spectral transmission spectrum of the sample (the reference sample or the measurement sample to be tested)) with the photodetector 20 using, for example, a light source including ultraviolet radiation of, for example, 290 thru 400 nm at predetermined wavelength gaps of, for example, 1 nm. Further, the temporal change measurement unit 34 measures a temporal change in the spectral transmission spectrum of the sample 1 by irradiating the light for a predetermined light irradiating time The temporal change measurement unit 34 may easily adjust a processing time or the like by measuring the temporal change in the spectral transmission spectrum at arbitrarily predetermined intervals. Therefore, the processing time for evaluation or the like may be shortened, when necessary. Further, the temporal change measurement unit 34 measures the temporal change of the spectral transmission spectrum of the sample 1. With this it is possible to calculate an in vitro predicted SPF that reflects photodegradation phenomenon of the sample due to the irradiated light.

The correlation setting unit 35 sets a correlation between the light irradiating time and the minimal erythema dose for a predetermined time unit based on the temporal change in the spectral transmission spectrum of the sample 1, which is obtained by the temporal change measurement unit 34, as a function of the computer 21. Specifically, the correlation setting unit 35 sets the correlation of the minimal erythema dose (MED) based on the temporal change in the spectral transmission spectrum using the result of measuring the temporal change in the spectral transmission spectrum. The correlation may be set by correlation equations described below or the like.

The minimal erythema dose used in the correlation setting unit 35 is calculated by multiplying light intensity of each wavelength by predetermined erythema factors (tendency to redness). With this, it is possible to calculate the minimal erythema dose (MED) with high accuracy. Values disclosed in for example, Non-Patent Document 2 (CIE Journal (1987) 6:1, 17-22) may be employed as the erythema factors. However, it is not limited in the present invention, and values disclosed in similar documents may be used.

The predicted SPF calculation unit 36 calculates the in vitro predicted SPF of the sample 1 as a function of the computer 21 based on a time until an accumulated minimal erythema dose, which is obtained by time integration based on the correlation set by the correlation setting unit 35, reaches 1 MED. Here, 1 MED means the light amount of ultraviolet radiation necessary to cause a minimal amount of erythema in a tested part of a volunteer at the in vivo SPF measurement site.

The predicted SPF calculation unit 36 uses at least one of item of data among the predicted in vitro SPF obtained from the predetermined samples, the light source intensity and a sample application amount applied on a skin substitute film in order to correct the predicted in vitro SPF.

Specifically, the predicted SPF calculation unit 36 uses a predetermined reference sample to carry out the processes in the above temporal change measurement unit 34 and the above correlation setting unit 35. Then, the predicted SPF calculation unit 36 calculates the predicted in vitro SPF in the reference sample using the time until the accumulated minimal erythema dose, which is the time integration of the minimal erythema doses based on the correlation set by the correlation setting unit 35, reaches 1 MED. The predicted in vitro SPF, which has been calculated as described above, may be stored in a storage unit 33 together with data of the used light source intensity and the reference sample application amount applied to the skin substitute film.

Next, the predicted SPF calculation unit 36 uses the measurement sample to calculate the predicted in vitro SPF in the measurement sample with the above-mentioned processes. The predicted SPF calculation unit 36 corrects the predicted in vitro SPF of the measurement sample using at least one of the predicted in vitro SPF, the light source intensity, the sample application amount or the like used for the reference sample.

Then, it becomes possible to calculate the predicted in vitro SPF which matches well the in vivo SPF with high accuracy. The predicted in vitro SPF in other reference samples may be corrected by the above-mentioned data when the predicted in vitro SPF in the other reference samples is obtained using the predicted in vitro SPF, the light source intensity and the reference sample application amount in the above-mentioned reference sample.

Further, the control unit 37, as a function of the computer 21, controls the entire structural part of the ultraviolet radiation protection effect evaluation apparatus 10. Specifically, the control unit 37 controls, based on, for example, a user's instructions from the input unit 31, measuring a temporal change in the spectral transmission spectrum, setting a correlation, and calculating and correcting predicted in vitro SPF. Further, the control unit 37, as a function of the computer 21, controls the light source 11 to be turned on or off.

<Hardware Structure of Ultraviolet Radiation Protection Effect Evaluation Apparatus 10>

As an example of the above-described ultraviolet radiation protection effect evaluation apparatus 10, an execution program (an evaluating program) which can be run by a computer to fulfill various functions may be generated, and the execution program may be installed in, for example, a general-purpose personal computer, a server or the like as the computer 21. Then, the ultraviolet radiation protection effect evaluation process of the embodiment may be realized.

The hardware structure of the computer which may realize the ultraviolet radiation protection effect evaluation process of the embodiment is described in reference to figures. FIG. 3 illustrates the hardware structure enabling the ultraviolet radiation protection effect evaluation process of the embodiment, as an example.

The computer illustrated in FIG. 3 includes an input device 41, an output device 42, a drive device 43, an auxiliary storage device 44, a memory device 45, a Central Processing Unit (CPU) 46 and a network connection device 47. These are mutually connected via a system bus B.

The input device 41 is provided for a user or the like to run programs and input various operation signals, and includes a keyboard, a pointing device such as a mouse or the like. The output device 42 includes a display for displaying various windows, data or the like necessary for operating the computer which carries out processes of the embodiment of the present invention. The output device 42 can display processes, results or the like obtained in running the program with the aid of a control program installed in the CPU 46.

In the embodiment, the execution program installed on the computer may be provided by a portable recording medium 48 such as a Universal Serial Bus (USB) and a CD-ROM. The recording medium 48 having the execution program recorded on it may be mounted on the drive device 43. The execution program included in the recording medium 48 is installed on an auxiliary storage device 44 via the driving device 43.

The auxiliary storage device 44 is a storage means such as a hard disk. The auxiliary storage device 44 can store the execution program of the embodiment of the present invention, and a control program, installed on the computer, or the like, thereby enabling to input or output these when necessary.

The memory device 45 stores the execution program, read out of the auxiliary storage device 44 by the CPU 46, or the like with the CPU 46. The memory device 45 includes a Read Only Memory (ROM), a Random Access Memory (RAM) or the like.

The CPU 46 controls entire processes of the computer such as various calculations, and inputs and outputs of data to and from various portions in the hardware structure to realize various processes of the ultraviolet radiation protection effect evaluation with the control program such as the operating system (OS) and the execution program stored in the memory device 45. The various information or the like necessary for running the program may be obtained from the auxiliary storage device 44. The results of the execution may be stored in the auxiliary storage device 44.

When the network connecting device 47 is connected to a communication network or the like, the network connecting device 47 may obtain the execution program from another terminal connected to a communication network, or provide execution results obtained by carrying out the execution program or the execution program itself of the embodiment to the other terminal or the like.

With the above-mentioned hardware structure, it is possible to carry out the processes of the ultraviolet radiation protection effect evaluation of the embodiment. Further, by installing the program on the general-purpose personal computer or the like, it is possible to easily realize the ultraviolet radiation protection effect evaluation of the embodiment.

<Evaluation Procedure of the Ultraviolet Radiation Protection Effect>

Next, the evaluation procedure of the ultraviolet radiation protection effect of the embodiment of the present invention is described in detail.

FIG. 4 illustrates the evaluation procedure of the ultraviolet radiation protection effect of the embodiment of the present invention, as an example. In the evaluation procedure illustrated in FIG. 4, light source intensity is first set in step S01. Specifically, when the light source intensity is set, the amount of light from a solar simulator (a simulated light source) is adjusted by a commercially-supplied radiometer (Type: 3D-600 or PMA-2100 manufactured by SolarLight Corporation). The amount of light is preferably in a range of about 0.5 thru 15 MED/min, more preferably in a range of about 1 thru 5 MED/min in conformity with the in vivo SPF measurement site.

Next, transmitted light through the reference sample is measured in step S02. Specifically, the reference sample may be applied on, for example, a skin substitute film. Here, the commercially-supplied polymethyl methacrylate (PMMA) plate having a size of, for example 50 mm×50 mm) or the like may be used as the skin substitute film. However, the present invention is not limited thereto. For example, it is preferable that the surface of the PMMA plate is processed by sandblasting so that the surface roughness (Sa) becomes about 1 thru 10 μm.

The reference sample (e.g., glycerin) is measured by a ratio of 0.75 mg/cm$^2$, for example. Thereafter, the reference sample is applied so as to be evenly spread on a surface of the PMMA plate by a finger with or without a finger cot for one minute. (The application work is disclosed in Non-Patent Document, "METHOD FOR THE IN VITRO DETERMI- NATION OF UVA PROTECTION PROVIDED BY SUNSCREEN PRODUCTS (COLIPA in vitro UVA measurement method)" 2007, pages 1-21, and so on. It is also possible to use an application device for applying the reference sample on the skin substitute film without using the finger with or without the finger cot. The application quantity is not specifically limited.

The reference sample to be applied is used not only as the skin substitute film but also as a blank of the measurement sample. Therefore, it is preferable to apply a liquid material having a transmittance of 50% or more in a wavelength range of at least 290 thru 400 nm. It is preferable to provide a predetermined drying time, for example about 15 minutes) before starting the measurement.

The ultraviolet radiation protection effect of the skin substitute film may be predicted using a so-called blank measurement. Therefore, the liquid material such as glycerin may be applied. However, samples of SPF4 and SPF15 may be used instead as a standard sample (a standard sample of which SPF is predetermined and which provides an identical SPF every time) in conformity with the measurement of in vivo SPF. Said differently, samples having a known and arbitrary SPF may be used as the reference sample. In this way, accuracy of the evaluation may be improved.

The measurement of the transmission light through the reference sample in step S02 of the above structure is described later.

Next, the results of the measurement of the transmission light obtained in step S02 are converted into the minimal erythema doses by each spectral transmission spectrum (a temporal change in the spectrum) under the temporal change by each of the times. Then, a correlation between the minimal erythema dose and the elapsed time are set in step S03. Specifically, the correlation such as correlation equations may be set based on the relationship between the minimal erythema dose obtained from plural temporal changes in the spectrum and the elapsed times, as an example.

The minimal erythema doses by each predetermined time are calculated based on the correlation such as the correlation equations set in step S03. The correlation between the accumulated minimal erythema doses and the elapsed times are set in step S04 from the result of the calculation. Content set in the correlation in steps S03 and S04 is described later.

In step S05, a predicted SPF in the reference sample is calculated based on the correlation between the accumulated minimal erythema doses and the elapsed times obtained in step S04 as described above. In step S05, the predicted SPF of the reference sample may be corrected using at least one of the old predicted SPF previously predicted in vitro SPF, the light source intensity and the application quantity of the reference sample applied on the skin substitute film. An example of step S05 is described later.

Thereafter, a test sample (a measurement sample) is applied on the skin substitute film, and transmission light through the test sample is measured in step S06. Specifically, the test sample is applied on the skin substitute film in a manner similar to the reference sample.

The test sample is measured by a ratio of 0.75 mg/cm$^2$, for example. Thereafter, the test sample is applied so as to be evenly spread on a surface of a PMMA plate by a finger with or without a finger cot for about one minute. It is also possible to use an application device for applying the test sample on the skin substitute film without using the finger with or without the finger cot. It is preferable to provide a predetermined drying time, for example about 15 minutes, before starting the measurement. An example of measuring the transmission light through the test sample in step S06 is described later. The application quantity of the test sample is not limited to the ratio of 0.75 mg/cm$^2$. The ratio may be increased as long as detection sensitivity of the measurement device allows.

Next, the results of the measurement of the transmission light obtained in step S06 are converted into minimal erythema doses by each spectral transmission spectrum (temporal change in the spectrum) under the temporal change by each of the times. Then, a correlation between the minimal erythema doses and the elapsed times are set in step S07. Specifically, in a manner similar to step S03, the correlation such as correlation equations may be set based on the relationship between the minimal erythema doses obtained from plural temporal change in the spectrum and the elapsed times, as an example.

The minimal erythema doses by each predetermined time are calculated based on the correlation such as the correlation equations set in step S07. The correlation between the accumulated minimal erythema doses and the elapsed times are set in step S08 from the result of the calculation. Contents of the correlation that have been set in steps S07 and S08 are described later.

In step S09, a predicted SPF in the test sample is calculated based on the correlation between the accumulated minimal erythema dose and the elapsed times obtained in step S08 as described above. In step S09, the predicted in vitro SPF is calculated using a time until the time integration of the minimal erythema based on the correlation reaches 1 MED.

In step S09, the predicted SPF may be corrected using at least one of the predicted in vitro SPF previously obtained in step S05, the light source intensity and the application quantity of the test sample applied on the skin substitute film. An example of step S09 is described later.

Next, steps S02 thru S09 are described in detail. FIG. 5A thru FIG. 5D illustrate measurement results of the reference sample in steps S02 thru S05. FIG. 6A thru FIG. 6D illustrate an example of the measurement results of a first sample (test sample A) in steps S06 thru S09. FIG. 7A thru FIG. 7D illustrate an example of the measurement results of a second sample (test sample B) in steps S06 thru S09. The results of the reference sample are illustrated in FIG. 5A thru FIG. 5D, and the results of the test samples (A, B) are illustrated in FIG. 6A thru FIG. 6D and FIG. 7A thru FIG. 7D.

In the measurement illustrated in FIG. 5A thru FIG. 7D, the light source intensity is determined to be 1 MED/min. As an example, the skin substitute film is a PMMA plate, the sample application quantity is 0.75 mg/cm$^2$, and the measurement time intervals are 1.5 min. Further, the reference sample is glycerin, as an example.

<Example of Measuring the Transmission Light Through the Samples in Steps S02 and S06>

Next, the example of the measurement of the transmission light through the samples in steps S02 and S06 is described. In the embodiment, the reference sample and the test samples are measured under continuous exposure to light having wavelengths of 290 thru 400 nm at intervals of 1 nm. Temporal changes in the spectrums from identical portions of the identical samples are measured for an arbitrary number of times at arbitrary intervals of the time.

Figure 5A:
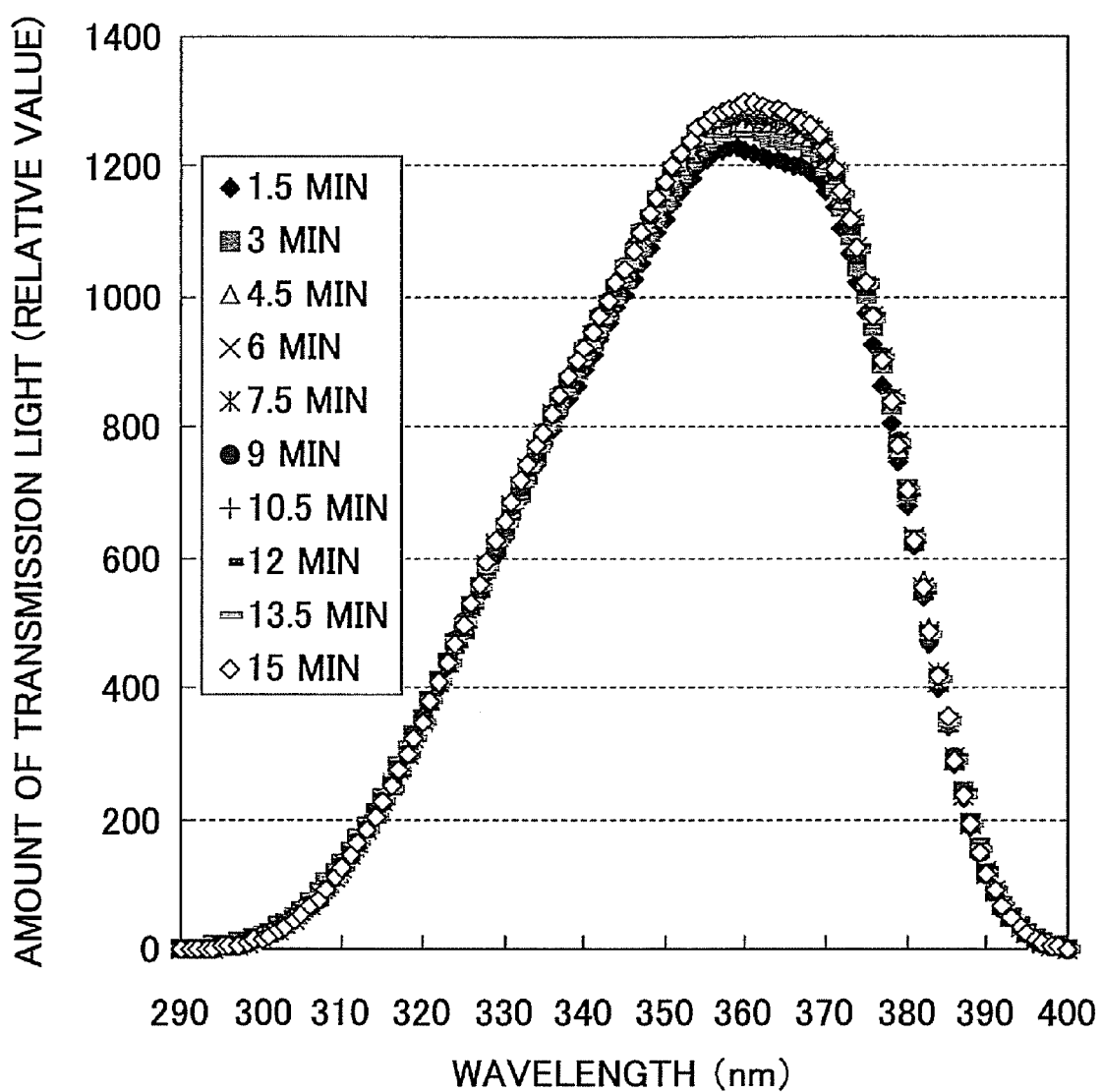
FIG. 5A illustrates measurement results (temporal change of spectra of a reference sample) of transmission light of the reference sample.
Figure 6A:
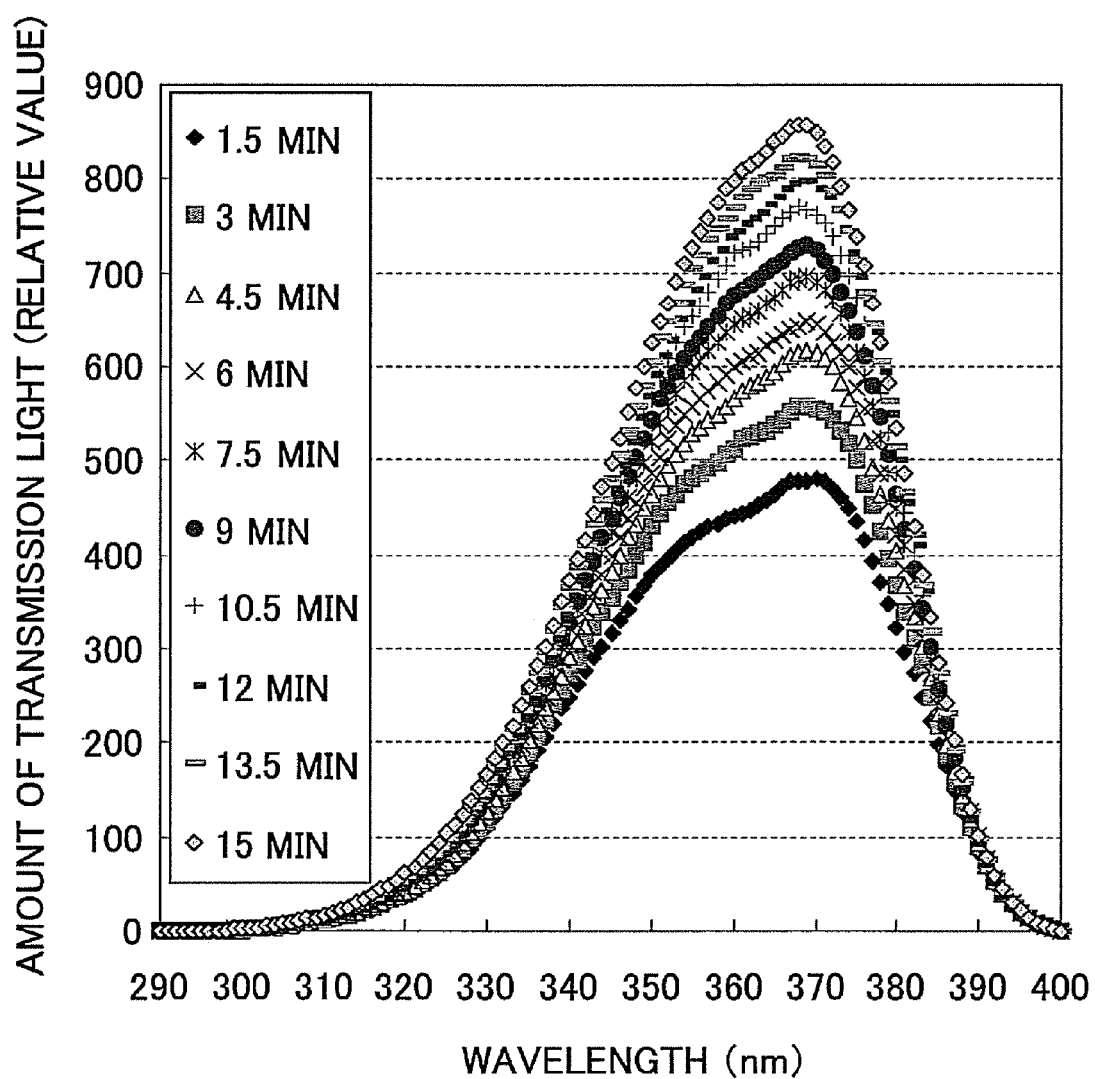
FIG. 6A illustrates measurement results (temporal change of spectra of test sample A) of transmission light of test sample A.
Figure 7A:
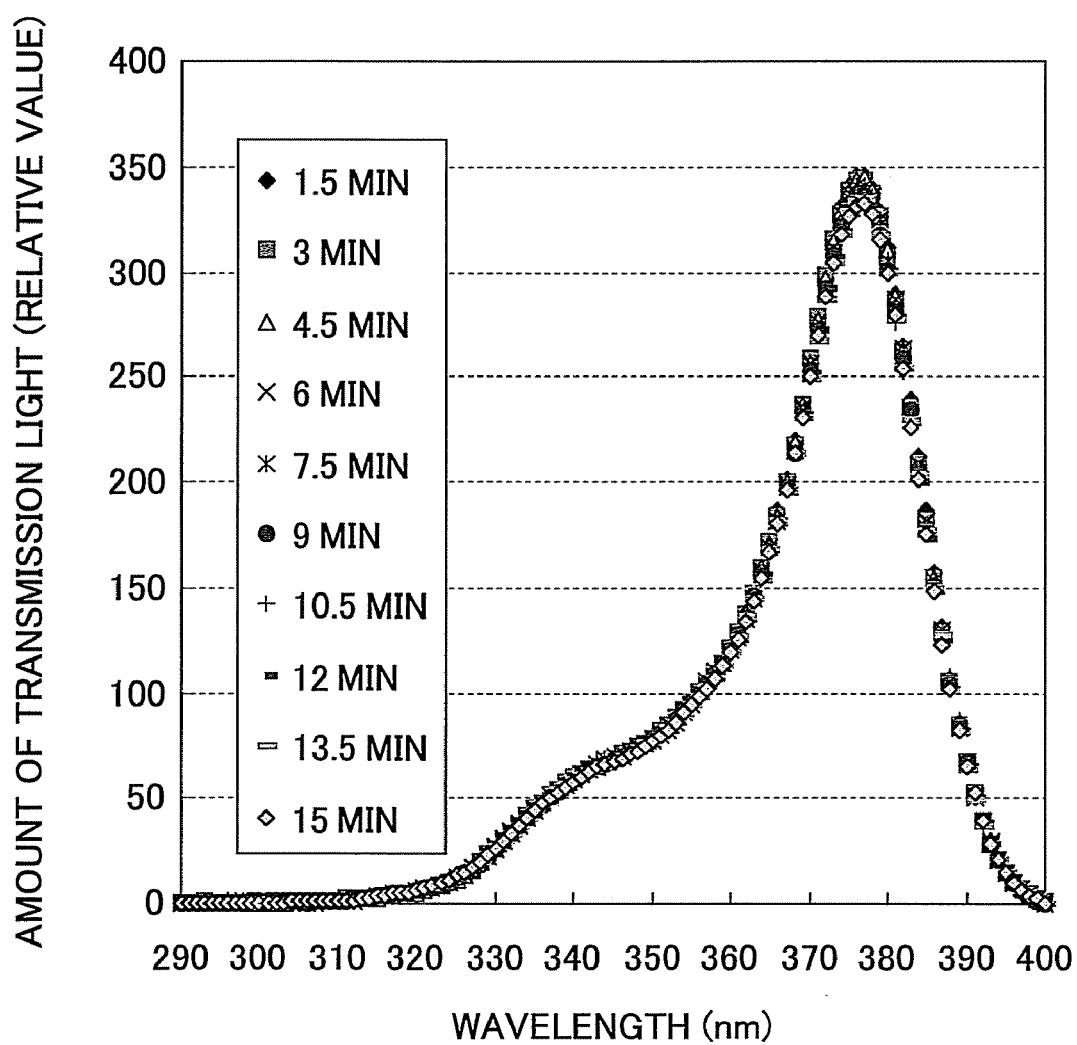
FIG. 7A illustrates measurement results (temporal change of spectra of test sample B) of transmission light of test sample B.

The measurement result (the temporal change in the spectrum from the reference sample) of the reference sample in step S02 is as illustrated in FIG. 5A. The measurement result (the temporal change in the spectrum from test sample A) of test sample A in step S06 is as illustrated in FIG. 6A. The measurement result (the temporal change in the spectrum from test sample B) of test sample B in step S06 is as illustrated in FIG. 7A. In FIG. 5A, FIG. 6A and FIG. 7A, the ordinate represents the amount of light transmission light, and the abscissa represents the wavelength (nm).

<Contents Set as the Correlation in Steps S03, S04, S05 and S08>

Next, the contents set as the correlations in steps S03, S04, S05 and S08 is described in detail.

The minimal erythema doses are calculated using, for example, the following Formula 1 based on the correlations between the minimal erythema doses and the elapsed times.

Formula 1

$$\text{MINIMAL ERYTHEMA DOSE} = \frac{\int_{290}^{400} E(\lambda)I_s(\lambda)d\lambda}{\int_{290}^{400} E(\lambda)I(\lambda)d\lambda / D} \quad (1)$$

In Formula 1, $E(\lambda)$ represents an action spectrum (Erythema action spectrum (CIE-1987)), $I_s(\lambda)$ represents light source intensity (Spectral irradiance of the sample layer) of the sample, $I(\lambda)$ represents the amount of the transmission light in each wavelength (Spectral irradiance of the UV source) of the sample, $d\lambda$ represents the wavelength intervals (Wavelength step) (1 nm in the embodiment), and D represents the used light source intensity (Intensity of the UV source (MED/min)).

Said differently, in Formula 1, the denominator represents the minimal erythema dose corresponding to 1 MED, and the numerator represents the minimal erythema dose of the sample. The correlation equation $Y_1$ (a primary expression of $Y_1=aX+b$) is derived from a relationship between the minimal erythema doses obtained from the plural temporal changes in the spectrums and the elapsed times. The reason for obtaining the correlation equation is to know a temporal change behavior of the sample. The Larger a gradient a is in the correlation equation, the more the sample is susceptible to photodegradation. The Smaller the gradient a is in the correlation equation, the less the sample is susceptible to photodegradation. It is important in this process to know a photodegradation behavior of the sample using the spectrums measured at arbitrary time intervals.

Figure 5B:
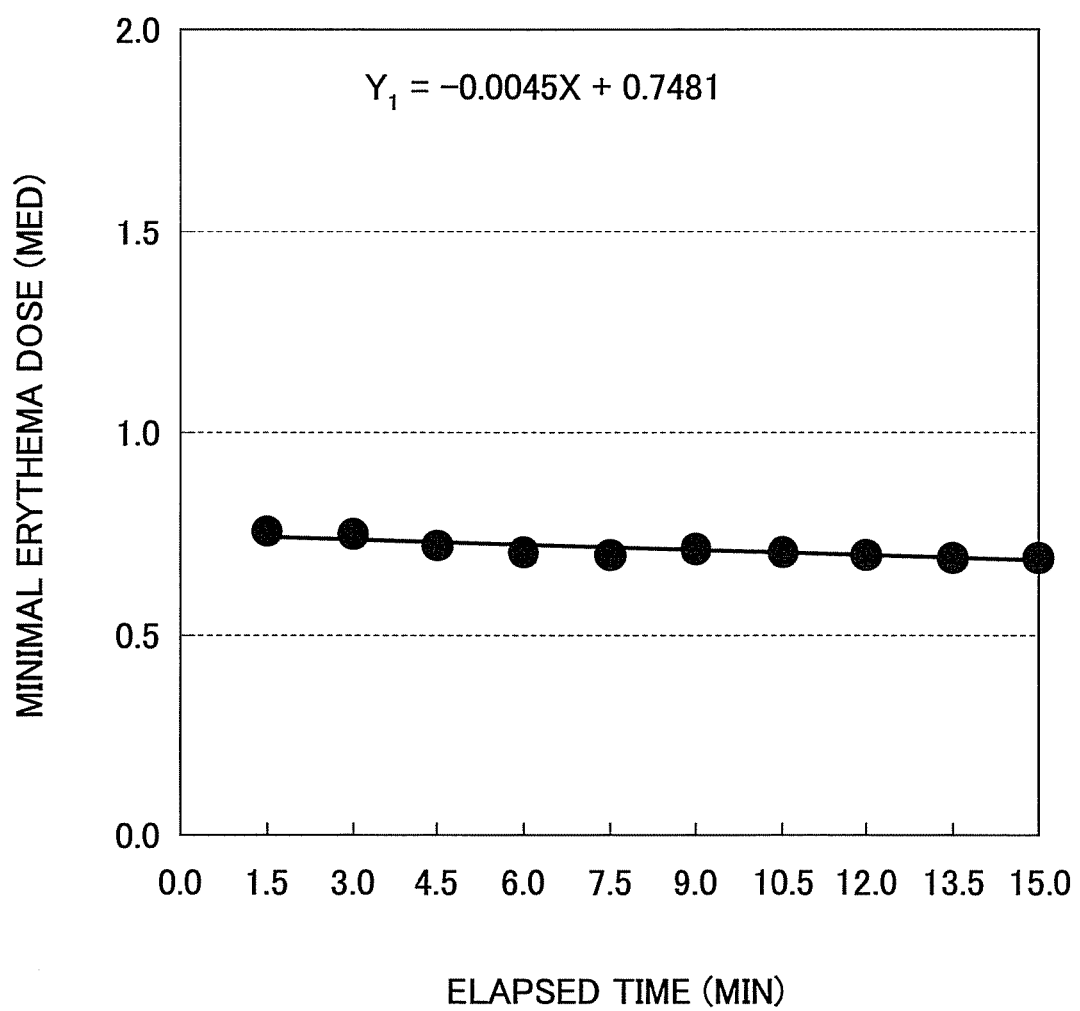
FIG. 5B illustrates measurement results (temporal change of minimal erythema dose of the reference sample) in the reference sample.
Figure 6B:
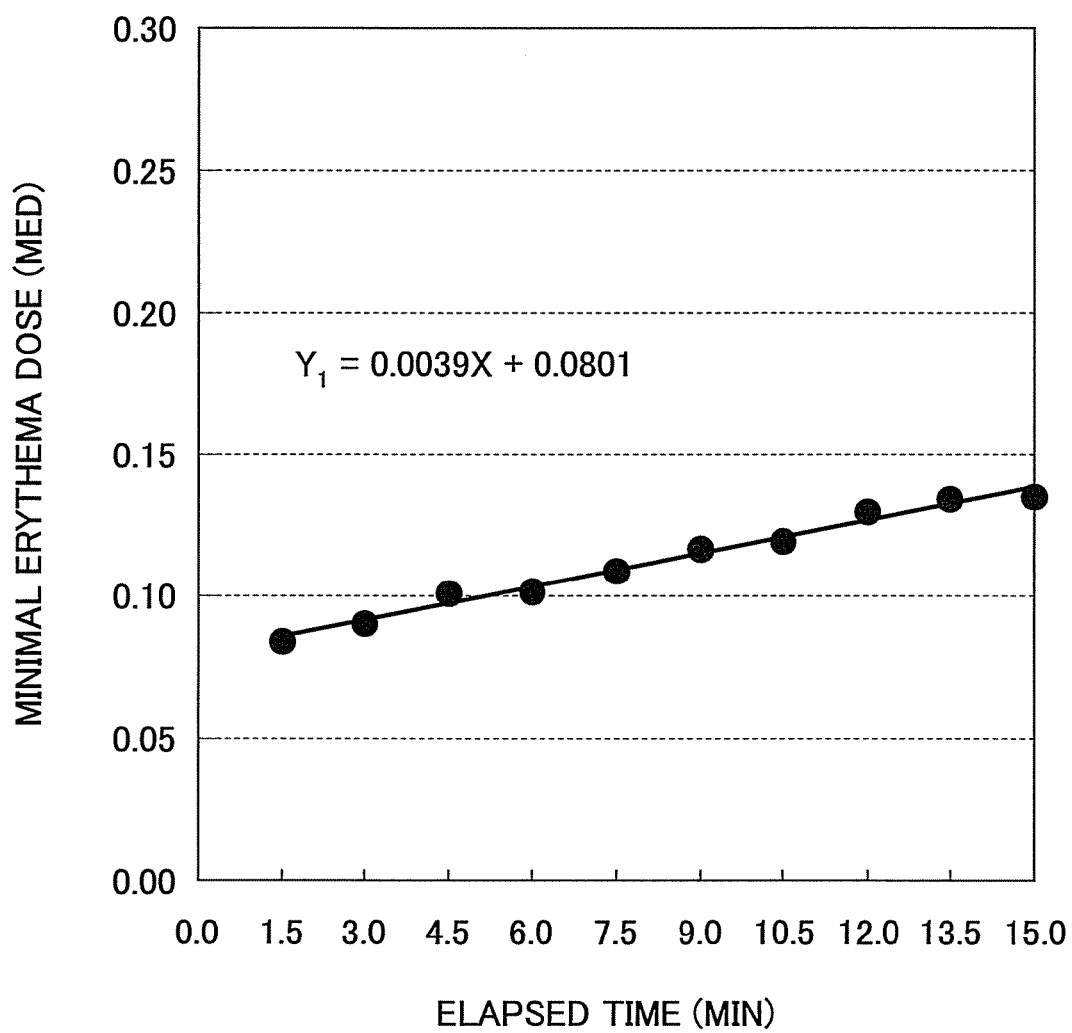
FIG. 6B illustrates measurement results (temporal change of minimal erythema dose of test sample A) in test sample A.
Figure 7B:
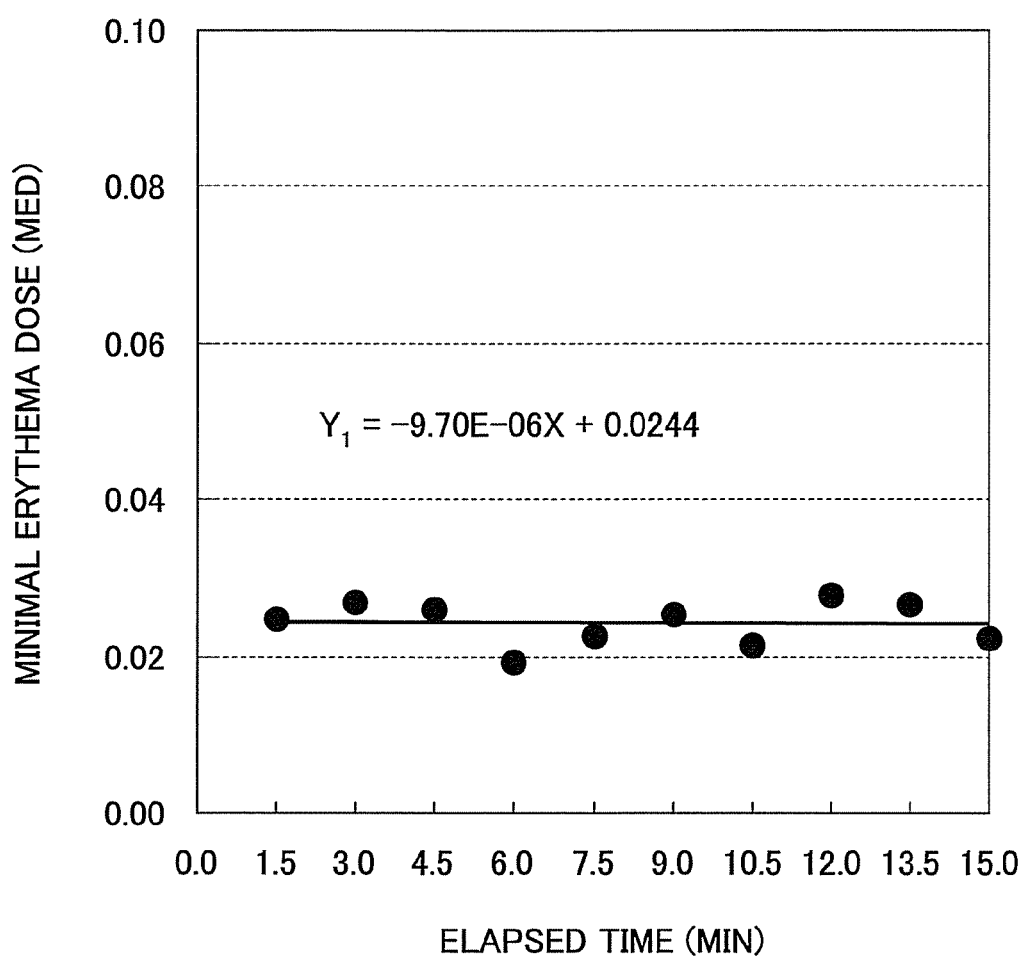
FIG. 7B illustrates measurement results (temporal change of minimal erythema dose of test sample B) in test sample B.

The measurement result (the temporal change of the minimal erythema dose in the reference sample) of the reference sample is as illustrated in FIG. 5B. The measurement result (the temporal change of the minimal erythema dose in test sample A) of test sample A is as illustrated in FIG. 6B. The measurement result (the temporal change of the minimal erythema dose in test sample B) of test sample B is as illustrated in FIG. 7B. In FIG. 5B, FIG. 6B and FIG. 7B, the ordinate represents the minimal erythema dose (MED), and the abscissa represents the elapsed time (min).

After processing the above steps, correlation equation $Y_1=-0.0045X+0.7481$ is derived from FIG. 5B, correlation equation $Y_1=0.0039X+0.0801$ is derived from FIG. 6B, and correlation equation $Y_1=-9.70E-06X+0.0244$ is derived from FIG. 7B.

In the correlation between the accumulated minimal erythema doses and the elapsed times in steps S04 and S08, values of the minimal erythema doses by each predetermined time (e.g., one minute) may be specifically calculated from the correlation equation $Y_1$ obtained from steps S03 and S07. The accumulated minimal erythema doses may be calculated by obtaining the time integration of the minimal erythema doses every one minute using the results of the correlations. Then, correlation equation $Y_2$ (exponential function of $Y_2=c(t_n)^d$) is derived.

The temporal changes in the spectrums are obtained in steps S03 and S07 at the arbitrary time intervals. For example, in order to obtain a time integration of the minimal erythema doses every one minute, the minimal erythema doses are converted into the minimal erythema doses every one minute. As used in setting the light source intensity, when light having intensity of 1 MED/min is irradiated from the light source, the minimal erythema dose becomes 1 MED after irradiating for one minute. Therefore, a unit of the time intervals for calculating the accumulated minimal erythema dose is preferably every one minute.

The minimal erythema doses and the accumulated minimal erythema doses of the reference sample, test sample A and test sample B are converted into data of every one minute as illustrated in FIG. 5C, FIG. 6C and FIG. 7C, respectively.

Figure 5D:
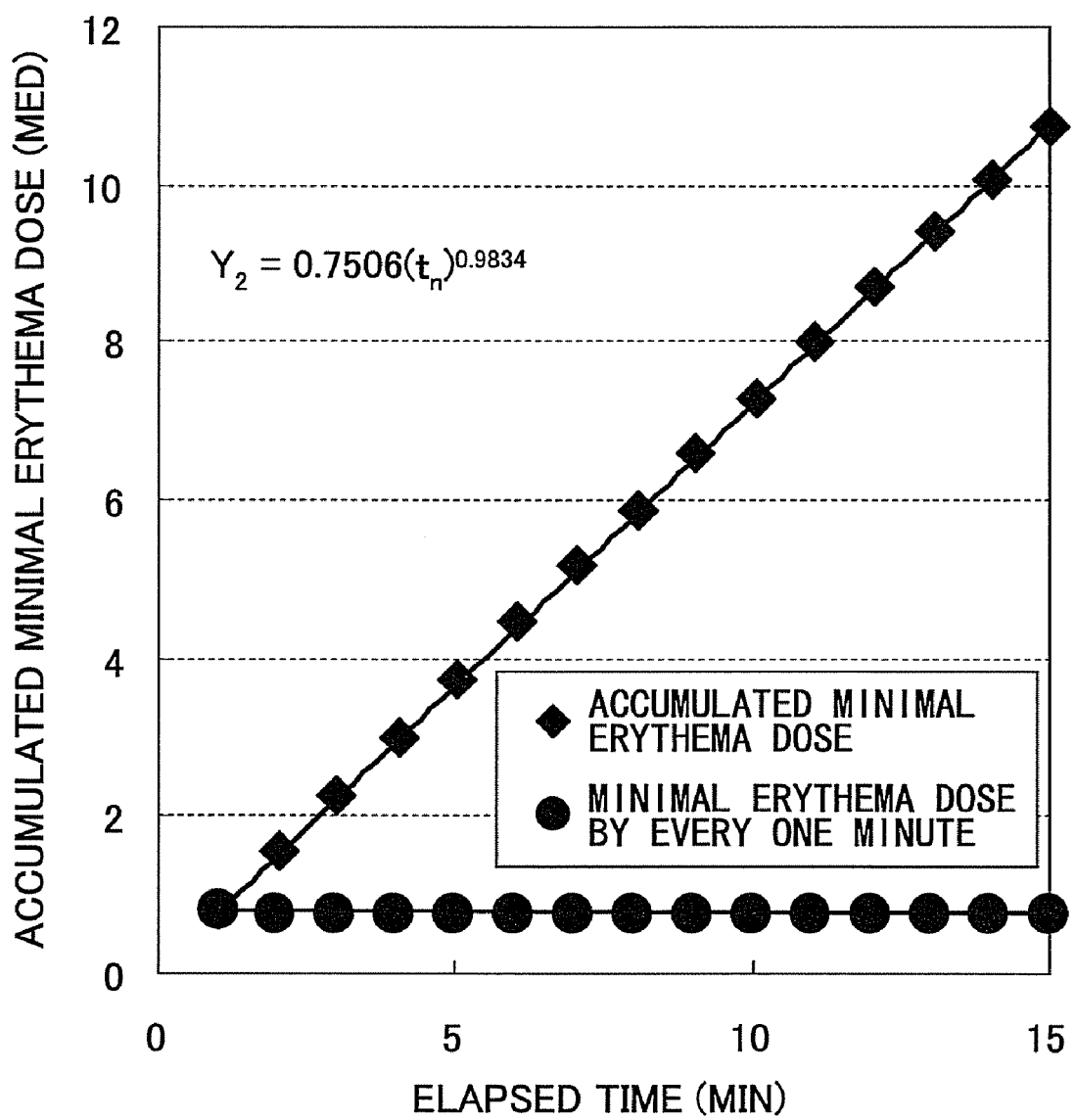
FIG. 5D illustrates the accumulated minimal erythema dose in the reference sample.
Figure 6D:
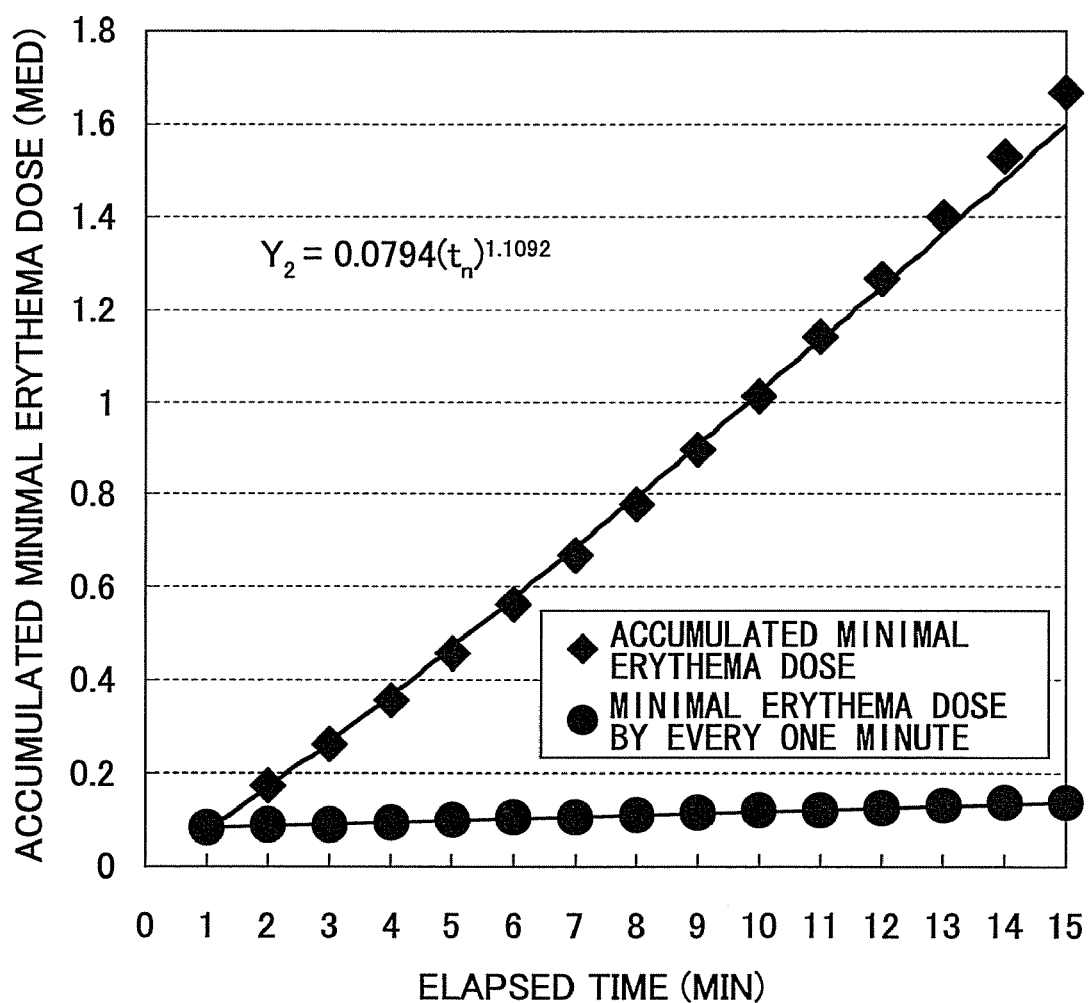
FIG. 6D illustrates the accumulated minimal erythema doses in test sample A.
Figure 7D:
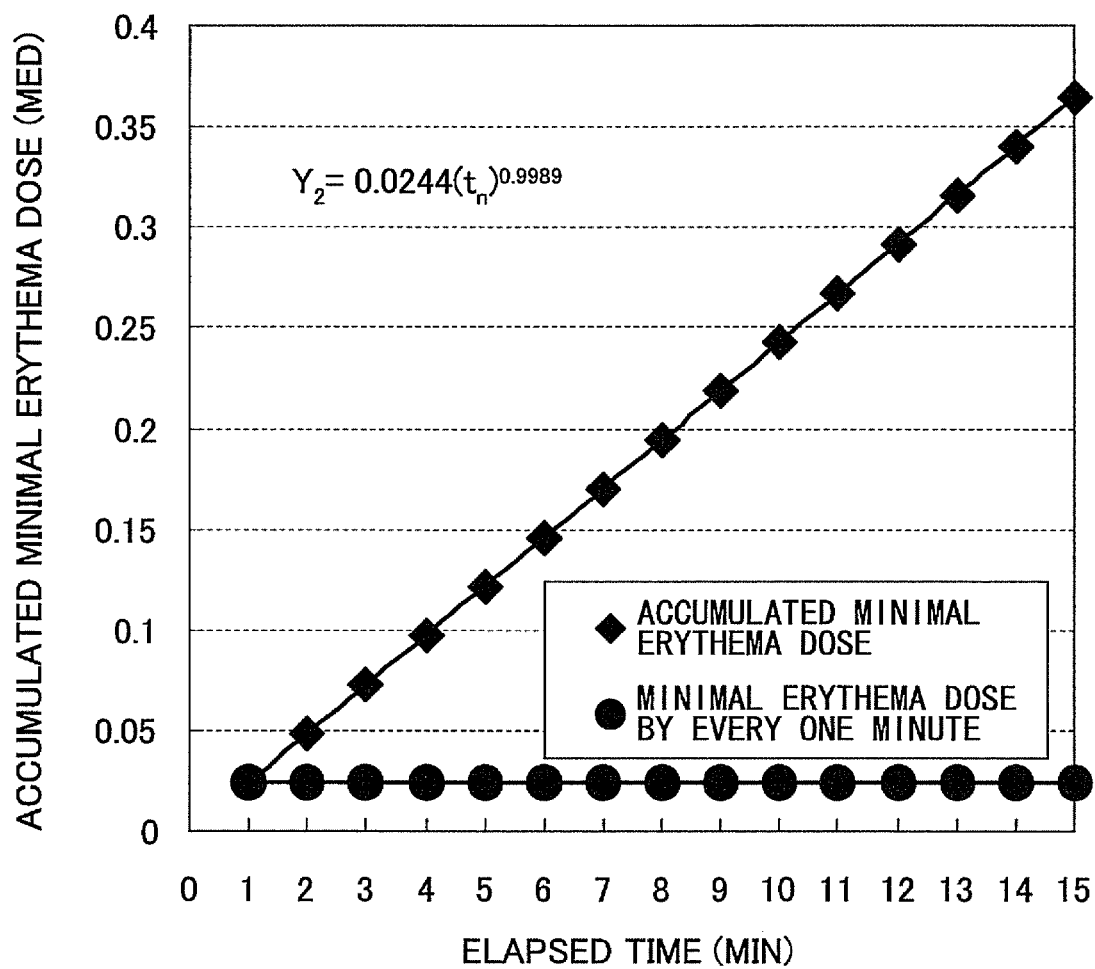
FIG. 7D illustrates the accumulated minimal erythema dose in the test sample B.

When the accumulated minimal erythema doses in the reference sample, test sample A and test sample B are allocated to the ordinate and the elapsed time (min) is allocated to the ordinate, FIG. 5D, FIG. 6D and FIG. 7D are respectively obtainable. Therefore, in case of FIG. 5D, correlation equation $Y_2=0.7506(t_n)^{0.9834}$ is derived. In the case of FIG. 6D, correlation equation $Y_2=0.0794\ (t_n)^{1.1092}$ is derived. In the case of FIG. 7D, correlation equation $Y_2=0.0244(t_n)^{0.9989}$ is derived. Therefore, in the case of FIG. 5D, correlation equation $Y_2=0.7506(t_n)^{0.9834}$ is derived. In the case of FIG. 6D, correlation equation $Y_2=0.0794\ (t_n)^{1.1092}$ is derived. In the case of FIG. 7D, correlation equation $Y_2=0.0244\ (t_n)^{0.9989}$ is derived.

The above correlation equations $Y_1$ and $Y_2$ are examples, and the present invention is not limited thereto. A correlation may be set by applying a function suitable for a sample to be used.

<Example of Calculation and Correction of the Predicted SPF in Step S05 and Step S09>

Next, the example of the calculation and correction of the predicted SPF is described. The SPF is a relative value indicating how many times an erythema prevention effect is larger in a portion on which a sample is applied than in a portion on which a sample is not applied. Therefore, it is possible to express the SPF with a number of times of amount of light irradiating the portion on which the sample is applied in comparison with an amount of light irradiating the portion on which the sample is not applied until minimal erythema dose of the portion on which the sample is not applied reaches 1 MED.

Therefore, a time duration while the accumulated minimal erythema dose for the portion on which the sample is applied reaches 1 MED is obtained in advance using the above correlation equation $Y_2$ in steps S04 and S08. A time integration value of the transmission light by each one minute, i.e. $Y_2=1$, is obtained as the accumulated minimal erythema dose. The time duration $t_n$ until the time integration value of the transmission light reaches 1 MED is obtained. When the used light source intensity is 1 MED/min, the time duration $t_n$ corresponds to $t_n$ MED.

An average of SPF (numbers of times) obtained using the above calculations preferably by three times or more is adopted as the predicted SPF in the sample. It is preferable to measure different PMMA plates on which an identical sample is applied in comparison with measuring three different portions of an identical PMMA plate on which the identical sample is applied.

It is possible to express the above-described calculation in a single equation of Formula 2.

Formula 2

$$\int_0^{t_n} \left( \int_{290}^{400} E(\lambda) I_s(\lambda, t) d\lambda \right) dt = \frac{\int_{290}^{400} E(\lambda) I(\lambda) d\lambda}{D} \quad (2)$$

In Formula 2, $E(\lambda)$ represents an action spectrum (Erythema action spectrum (CIE-1987)), $I_S(\lambda)$ represents light source intensity (Spectral irradiance of the sample layer) of the sample, $I(\lambda)$ represents the amount of the transmission light in each wavelength (Spectral irradiance of the UV source) of the sample, $d\lambda$ represents the wavelength intervals (Wavelength step) (1 nm in the embodiment), dt represents the time intervals (Time step) (1 min in the embodiment), $t_n$ represents the elapsed time (Irradiation time), and D represents the used light source intensity (Intensity of the UV source (MED/min)). The used light source intensity D is light source intensity obtained by irradiating the spectrometer and the photodetector without interposing the reference sample and the test sample.

The left-hand side of Formula 2 represents the time integration of the minimal erythema doses of the portion on which the sample is applied (a time function is applied to the spectrum in the sample), and the right-hand side represents the minimal erythema dose of 1 MED in the portion on which the sample is not applied. The above-described equations are only examples. The content of setting the correlation in the present invention is not limited to the above.

Next, when it is necessary to correct the predicted SPF calculated above, the correction is carried out by using at least one of the light source intensity, the predicted SPF and the sample application quantity in the embodiment. Specifically, the correction using the light source intensity uses the used light source intensity (D MED/min). The used light source intensity D is substituted into Formula 3 to thereby calculate predicted SPFs of the sample.

Formula 3

$$\text{in vitro } SPF_s = t_n \times D \quad (3)$$

The SPFs designates the predicted SPF of the test sample (SPF of the sample), $t_n$ designates the elapsed time (Irradiation time), and D designates the used light source intensity (intensity of the UV source) (MED/min).

In the correction using the light source intensity, it is possible to make the time until the accumulated minimal erythema dose in the sample reaches 1 MED shorter as the light source intensity is stronger. Therefore, if the photodegradation behavior of the sample obeys the light reciprocity law (said differently, an identical behavior is demonstrated as long as the product of light intensity and an irradiation time is constant, and an identical result is obtainable when strong light irradiates for a short time and when weak light irradiates for a long time), it is necessary to multiply the elapsed time ($t_n$) by the light source intensity (D MED/min). Therefore, on the premise that the light reciprocity law is in effect, the light source intensity that is considered the stronger light source intensity causes a minimal amount of erythema to be 1 MED within a shorter time.

The correction using the predicted SPF in the reference sample is calculated in compliance with Formula 4 below so that the reference sample (i.e., a skin substitute film or glycerin) is corrected as in vitro SPF.

Formula 4

$$\text{in vitro SPF} = \text{in vitro SPF}_s - (\text{in vitro SPF}_r - 1) \quad (4)$$

The SPFs designates the predicted SPF in the test sample (SPF of the sample), and the SPFr designates a predicted SPF of the reference sample (SPF of the reference (PMMA-DG: glycerin)).

In Formula 4, "a value subtracting 1 from SPF in the reference sample" is subtracted from "SPF in the sample". Because SPF is a criteria in which 1 is the minimum value, it is considered that SPF more than 1 may be corrected. Therefore, this idea that SPF more than 1 may be corrected is reflected to the minimal erythema dose by delaying the time as much.

The correction using the predicted SPF in the reference sample is not limited to Formula 4. SPF in the sample (SPFs) may be divided by SPF of the reference sample (SPFr).

Formula 5

$$\text{in vitro } SPF = \frac{\text{in vitro } SPF_s}{\text{in vitro } SPF_r} \quad (5)$$

Thus, the correction for the skin substitute film can be done by correcting an amount multiplied in the predicted SPF.

For example, referring to FIG. 5D, the predicted SPF of the reference sample (SPFr) is 1.34 corresponding to $t_n$ when the correlation equation $Y_2=1$ is established. Further, SPFr=1.34 is established since the light source intensity is 1 MED/min. In a manner similar to the above, when the SPF is measured three times in total, the SPFr is obtained as 1.34, 1.38 and 1.29. Then, the average of SPFr=1.34 is obtained.

Referring to FIG. 6D, the predicted SPF of test sample A (SPFs) is 9.81 corresponding to $t_n$ when the correlation equation $Y_2=1$ is established. Further, SPFs=9.81 is established since the light source intensity is 1 MED/min. In a manner similar to the above, when the SPFs is measured three times in total, the SPFs is obtained as 9.81, 10.12 and 9.55. Then, the average of SPFs=9.83 is obtained. Therefore, in vitro SPF in test sample A becomes 9.83−(1.34−1)=9.49 using the above Formula 4.

Referring to FIG. 6D, the predicted SPF of test sample B (SPFs) is 41.15 corresponding to $t_n$ when the correlation equation $Y_2=1$ is established. Further, SPFs=41.15 is established since the light source intensity is 1 MED/min. In a manner similar to the above, when the SPFs is measured three times in total, the SPFs is obtained as 41.15, 39.29 and 38.21. Then, the average of SPFs=39.55 is obtained. Therefore, in vitro SPF in test sample A becomes 39.55−(1.34−1)=39.21 using the above Formula 4.

The application quantity in the present evaluation method of the embodiment of the present invention is corrected using a sample application quantity of 0.75 mg/cm$^2$. Since the measurement of in vivo SPF is carried out using a sample application quantity of 2.0 mg/cm$^2$, it is necessary to correct the application quantity in order to predict an in vitro SPF in conformity with the in vivo SPF.

The above correction method is an example and not limiting. For example, it is disclosed in a known document (Non-Patent Document "Skin Pharmacology and Physiology 2007; 20: 57-64") a linear relationship between an application quantity and an in vivo SPF. In consideration of this linear relationship, (2.0 mg/cm$^2$)/(0.75 mg/cm$^2$)≈2.67 is obtainable. By multiplying the predicted SPF by this 2.67, the SPF can be corrected. However, the present invention is not limited thereto.

In the above-mentioned steps S02 thru S05, the calculation and correction of the predicted SPF in the reference sample may be done in advance, and the results of the calculation and correction may be stored. Thereafter, the stored result may be used to process steps S06 thru S09 in evaluating the ultraviolet radiation protection effect.

<Evaluation of the Correlation>

Here, the correlation between the in vitro SPF and the in vivo SPF is described in reference to figures.

Figure 8:
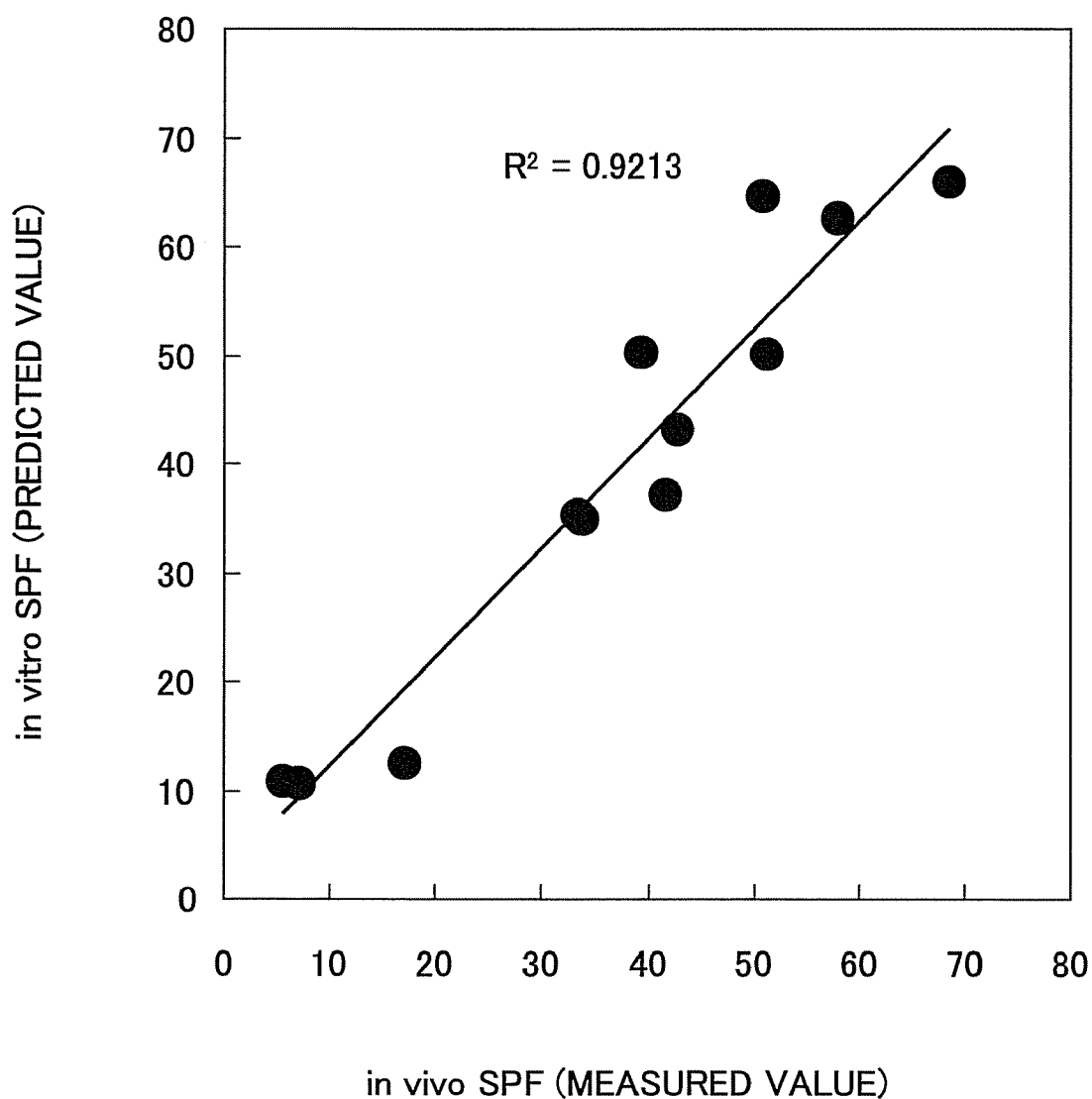
FIG. 8 is a diagram illustrating correlation between in vivo SPF and in vitro SPF as an example.

FIG. 8 is a diagram illustrating the correlation between the in vivo SPF and the in vitro SPF as an example. In FIG. 8, the ordinate represents the in vitro SPF (predicted value), and the abscissa represents in vivo SPF (measured value).

FIG. 8 illustrates an in vivo SPF measurement obtained by physically measuring the effects of ultraviolet radiation on actual skin along with an in vitro SPF. Referring to FIG. 8, the correlation is good and proved to fit reality.

In the embodiment, although time intervals of measuring the light source intensity and spectrum can be arbitrarily set, it is preferable to set the time intervals such that the accumulated minimal erythema dose up to the final measurement of the spectrum exceeds 1 MED. On the contrary, it is not preferable that the accumulated minimal erythema dose exceeds 1 MED until the first one or two spectrums are measured. Because the predicted value is calculated by converting the acquired spectrum into a minimal erythema dose and deriving an arithmetic expression, it is preferable to increase the number of effective spectrums to as many as possible. Specifically, it is preferable to measure the spectrums 5 times or more. Therefore, it is preferable to adjust the light source intensity, the measurement time intervals, the number of times of the measurements depending on the samples.

According to the embodiment of the present invention, it is possible to realize a highly accurate evaluation of an ultraviolet radiation protection effect using in vitro measurement having a high correlation with in vivo SPF even for samples having high SPF by reflecting the photodegradation phenomenon of the samples caused due to irradiated light.

Specifically, the in vitro SPF can be evaluated based on a continuous irradiation time until the accumulated minimal erythema dose becomes 1 MED in a manner similar to actual skin. Conventionally, accurate measurement of a high SPF was difficult. The measurement of the embodiment can be applied to products having high SPF (e.g., products of an SPF of 50 or more). It is possible to provide an ultraviolet radiation protection effect evaluation apparatus which can trace temporal changes in a sample with high sensitivity even though the sample causes a photodegradation phenomenon.

Further, it is possible to reflect the photodegradation phenomenon on the prediction of the in vitro SPF by using the ultraviolet radiation protection effect evaluation apparatus with high sensitivity. Further, the in vitro SPF evaluation method is excellent in the correlation with the in vivo SPF, and may realistically restage ultraviolet radiation onto skin.

Although there has been described the embodiment of the present invention, the present invention is not limited to the above embodiment, and various modifications and changes are possible in the scope of the present invention described in the claims.

The international application is based on Japanese Priority Patent Application No. 2007-271743 filed on Oct. 18, 2007, the entire contents of which are hereby incorporated herein by reference.

The invention claimed is:

1. An evaluating method for evaluating an ultraviolet radiation protection effect in a measurement sample comprising:
    a first step of measuring a temporal change of a spectral transmission spectrum in the measurement sample within a predetermined wavelength range at predetermined wavelength intervals by irradiating the measurement sample with light including ultraviolet radiation from a light source under a predetermined light irradiating condition;
    a second step of setting a correlation between a light irradiating time and minimal erythema doses by predetermined time intervals, which minimal erythema doses are obtained by dividing minimal erythema doses of the measurement sample by a minimal erythema dose corresponding to 1 MED, based on the temporal change of the spectral transmission spectrum obtained in the first step;
    a third step of calculating a predicted in vitro SPF (Sun Protection Factor) in the measurement sample using a time until an accumulated minimal erythema dose that is obtained as a time integration of the minimal erythema doses based on the correlation obtained in the second step reaches 1 MED (Minimum Erythema Dose).

2. The evaluating method according to claim 1, wherein, in the first step, the temporal change of the spectral transmission spectrum is measured at predetermined time intervals.

3. The evaluating method according to claim 1, wherein, in the first step, the temporal change of the spectral transmission spectrum is caused by photodegradation of the spectral transmission spectrum.

4. The evaluating method according to claim 1, wherein, the predicted in vitro SPF in the measurement sample is corrected using at least one item of data of a predicted in vitro SPF which is obtained from a predetermined reference sample, light source intensity of the light source, and an application quantity applied on a skin substitute film.

5. The evaluating method according to claim 4, wherein, in the third step, a liquid material having a transmittance of 50% or more is applied on the skin substitute film at least in the predetermined Wavelength range in the first step to be used as the predetermined reference sample.

6. The evaluating method according to claim 4, wherein, in the third step, a sample of which in vivo SPF is known is used as the predetermined reference sample at least in the predetermined wavelength range in the first step.

7. The evaluating method according to claim 1, wherein, in the third step, the predicted in vitro SPF in the measurement sample of 1 MED is calculated based on light source intensity when the predetermined light irradiating condition is that the light irradiates only from the light source.

8. An evaluating apparatus that evaluates an ultraviolet radiation protection effect in a measurement sample, the evaluating apparatus comprising:
    a temporal change measurement unit configured to measure a temporal change of a spectral transmission spectrum in the measurement sample within a predetermined wavelength range at predetermined wavelength intervals by irradiating the measurement sample with light including ultraviolet radiation from a light source under a predetermined light emission condition;

a correlation setting unit configured to set a correlation between a light irradiating time and minimal erythema doses by predetermined time intervals, which minimal erythema doses are obtained by dividing minimal erythema doses of the measurement sample by a minimal erythema dose corresponding to 1 MED (Minimum Erythema Dose), based on the temporal change of the spectral transmission spectrum obtained by the temporal change measurement unit; and a predicted SPF (Sun Protection Factor) calculation unit configured to calculate a predicted in vitro SPF in the measurement sample using a time until an accumulated minimal erythema dose that is obtained as a time integration of the minimal erythema doses based on the correlation obtained by the correlation setting unit reaches 1 MED.

9. The evaluating apparatus according to claim 8, wherein the temporal change measurement unit measures the temporal change of the spectral transmission spectrum at predetermined time intervals.

10. The evaluating apparatus according to claim 8, wherein the temporal change measurement unit measures the temporal change of the spectral transmission spectrum caused by photodegradation of the spectral transmission spectrum.

11. The evaluating apparatus according to claim 8, wherein the predicted SPF calculation unit corrects the predicted in vitro SPF in the measurement sample using at least one item of data of a predicted in vitro SPF which is obtained from a predetermined reference sample, light source intensity of the light source, and an application quantity applied on a skin substitute film.

12. The evaluating apparatus according to claim 11, wherein the predicted SPF calculation unit uses, as the predetermined reference sample, a liquid material having a transmittance of 50% or more applied on the skin substitute film at least in the predetermined wavelength range used in the temporal change measurement unit.

13. The evaluating apparatus according to claim 11, wherein the predicted SPF calculation unit uses, as the predetermined reference sample, a sample, of which in vivo SPF is known, at least in the predetermined wavelength range used in the temporal change measurement unit.

14. The evaluating apparatus according to claim 8, wherein the predicted SPF calculation unit calculates the predicted in vitro SPF in the measurement sample of 1 MED based on light source intensity when a predetermined light irradiating condition is that the light irradiates only from the light source.

15. A non-transitory computer-readable recording medium storing an evaluating computer program that evaluates an ultraviolet radiation protection effect in a measurement sample, the evaluating computer program representing a sequence of instructions, which when executed by a computer, the instructions cause the computer to perform:

a first step of measuring a temporal change of a spectral transmission spectrum in the measurement sample within a predetermined wavelength range at predetermined wavelength intervals by irradiating the measurement sample with light including ultraviolet radiation from a light source under a predetermined light irradiating condition;

a second step of setting a correlation between a light irradiating time and minimal erythema doses by predetermined time intervals, which minimal erythema doses are obtained by dividing minimal erythema doses of the measurement sample by a minimal erythema dose corresponding to 1 MED (Minimum Erythema Dose) based on the temporal change of the spectral transmission spectrum obtained in the first step;

a third step of calculating a predicted in vitro SPF (Sun Protection Factor) in the measurement sample using a time until an accumulated minimal erythema dose that is obtained as a time integration of the minimal erythema doses based on the correlation obtained in the second step reaches 1 MED.

* * * * *